US011096591B2

(12) United States Patent
Miesel et al.

(10) Patent No.: US 11,096,591 B2
(45) Date of Patent: Aug. 24, 2021

(54) DETERMINATION OF SLEEP QUALITY FOR NEUROLOGICAL DISORDERS

(71) Applicant: Medtronic, Inc., Minneapolis, MN (US)

(72) Inventors: Keith A. Miesel, St. Paul, MN (US); Kenneth T. Heruth, Edina, MN (US); Jonathan C. Werder, Corcoran, MN (US); Steve R. LaPorte, San Antonio, TX (US); Nina M. Graves, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 224 days.

(21) Appl. No.: 16/365,731

(22) Filed: Mar. 27, 2019

(65) Prior Publication Data
US 2019/0217098 A1 Jul. 18, 2019

Related U.S. Application Data

(60) Division of application No. 14/247,923, filed on Apr. 8, 2014, now Pat. No. 10,300,283, which is a (Continued)

(51) Int. Cl.
*A61N 1/36* (2006.01)
*A61M 5/172* (2006.01)
(Continued)

(52) U.S. Cl.
CPC .......... *A61B 5/0205* (2013.01); *A61B 5/1116* (2013.01); *A61B 5/1118* (2013.01);
(Continued)

(58) Field of Classification Search
CPC ... A61B 5/0205; A61B 5/1116; A61B 5/1118; A61B 5/4815; A61B 5/4818;
(Continued)

(56) References Cited

U.S. PATENT DOCUMENTS 4,297,685 A 10/1981 Brainard, II
4,550,736 A 11/1985 Broughton et al.
(Continued)

FOREIGN PATENT DOCUMENTS

DE 19831109 A1 1/2000
DE 10024103 A1 11/2001
(Continued)

OTHER PUBLICATIONS

Aminian et al. "Physical Activity Monitoring Based on Accelerometry: Validation and Comparison with Video Observation," Medical & Biological Engineering & Computing, vol. 37, No. 2, pp. 304-308 May 1999.
(Continued)

*Primary Examiner* — Navin Natnithithadha
*Assistant Examiner* — Sunita Reddy
(74) *Attorney, Agent, or Firm* — Shumaker & Sieffert, P.A.

(57) ABSTRACT

A device determines values for one or more metrics that indicate the quality of a patient's sleep based on sensed physiological parameter values. Sleep efficiency, sleep latency, and time spent in deeper sleep states are example sleep quality metrics for which values may be determined. The sleep quality metric values may be used, for example, to evaluate the effectiveness of a therapy delivered to the patient by a medical device. In some embodiments, determined sleep quality metric values are automatically associated with the therapy parameter sets according to which the medical device delivered the therapy when the physiological parameter values were sensed, and used to evaluate the effectiveness of the various therapy parameter sets. The medical device may deliver the therapy to treat a non-respiratory neurological disorder, such as epilepsy, a move-
(Continued)

ment disorder, or a psychological disorder. The therapy may be, for example, deep brain stimulation (DBS) therapy.

7 Claims, 17 Drawing Sheets

Related U.S. Application Data continuation of application No. 11/591,286, filed on Oct. 31, 2006, now Pat. No. 8,725,244, which is a continuation-in-part of application No. 11/081,811, filed on Mar. 16, 2005, now abandoned, which is a continuation-in-part of application No. 10/826,925, filed on Apr. 15, 2004, now Pat. No. 7,717,848.

(60) Provisional application No. 60/785,678, filed on Mar. 24, 2006, provisional application No. 60/553,783, filed on Mar. 16, 2004.

(51) Int. Cl.
*A61B 5/00* (2006.01)
*A61B 5/11* (2006.01)
*A61M 5/142* (2006.01)
*A61B 5/0205* (2006.01)
*A61B 3/113* (2006.01)
*A61B 5/08* (2006.01)
*A61B 5/145* (2006.01)
*A61N 1/365* (2006.01)
*A61N 1/372* (2006.01)
*A61B 5/369* (2021.01)

(52) U.S. Cl.
CPC .......... *A61B 5/4812* (2013.01); *A61B 5/4815* (2013.01); *A61B 5/4818* (2013.01); *A61M 5/14276* (2013.01); *A61M 5/1723* (2013.01); *A61N 1/36064* (2013.01); *A61N 1/36067* (2013.01); *A61N 1/36082* (2013.01); *A61N 1/36135* (2013.01); *A61B 3/113* (2013.01); *A61B 5/0031* (2013.01); *A61B 5/0816* (2013.01); *A61B 5/145* (2013.01); *A61B 5/369* (2021.01); *A61B 5/686* (2013.01); *A61B 5/6814* (2013.01); *A61B 5/6823* (2013.01); *A61B 5/6825* (2013.01); *A61B 2562/0219* (2013.01); *A61N 1/36025* (2013.01); *A61N 1/36071* (2013.01); *A61N 1/36521* (2013.01); *A61N 1/36542* (2013.01); *A61N 1/36557* (2013.01); *A61N 1/37247* (2013.01)

(58) Field of Classification Search
CPC ..... A61B 5/686; A61B 5/6814; A61B 5/6823; A61B 5/6825; A61B 3/113; A61B 5/0031; A61B 5/0476; A61B 5/0816; A61B 5/145; A61B 2562/0219; A61N 1/36064; A61N 1/36067; A61N 1/36135; A61N 1/36082; A61N 1/36025; A61N 1/37247; A61N 1/36071; A61N 1/36521; A61N 1/36542; A61N 1/36557; A61M 5/14276; A61M 5/1723
USPC .................................................... 600/26–28
See application file for complete search history.

(56) References Cited

U.S. PATENT DOCUMENTS

| | | |
|---|---|---|
| 4,771,780 A | 9/1988 | Sholder |
| 4,776,345 A | 10/1988 | Cohen et al. |
| 4,846,195 A | 7/1989 | Alt |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,509,927 A | 4/1996 | Epstein et al. |
| 5,514,162 A | 5/1996 | Bornzin et al. |
| 5,591,216 A | 1/1997 | Testerman et al. |
| 5,593,431 A | 1/1997 | Sheldon |
| 5,622,428 A | 4/1997 | Bonnet |
| 5,645,053 A | 7/1997 | Remmers et al. |
| 5,683,432 A | 11/1997 | Goedeke et al. |
| 5,713,923 A | 2/1998 | Ward et al. |
| 5,732,696 A | 3/1998 | Rapoport et al. |
| 5,782,884 A | 7/1998 | Stotts et al. |
| 5,787,884 A | 8/1998 | Tovey |
| 5,814,093 A | 9/1998 | Stein |
| 5,851,193 A | 9/1998 | Arikka |
| 5,833,709 A | 11/1998 | Rise et al. |
| 5,895,371 A | 4/1999 | Levitas et al. |
| 5,904,708 A | 5/1999 | Goedeke |
| 5,904,861 A | 5/1999 | Ban et al. |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,999,846 A | 12/1999 | Pardey et al. |
| 6,006,124 A | 12/1999 | Fischell et al. |
| 6,044,297 A | 3/2000 | Sheldon et al. |
| 6,045,513 A | 4/2000 | Stone et al. |
| 6,059,576 A | 5/2000 | Brann |
| 6,091,973 A | 7/2000 | Colla et al. |
| 6,094,598 A | 7/2000 | Elsberry et al. |
| 6,095,991 A | 8/2000 | Krausman et al. |
| 6,102,874 A | 8/2000 | Stone et al. |
| 6,120,467 A | 9/2000 | Schallhorn |
| 6,126,611 A | 10/2000 | Bourgeois et al. |
| 6,128,534 A | 10/2000 | Park et al. |
| 6,157,857 A | 12/2000 | Dimpfel |
| 6,161,095 A | 12/2000 | Brown |
| 6,165,143 A | 12/2000 | Van Lummel |
| 6,227,203 B1 | 5/2001 | Rise et al. |
| 6,259,948 B1 | 7/2001 | Florio et al. |
| 6,273,856 B1 | 8/2001 | Sun et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,315,740 B1 | 11/2001 | Singh |
| 6,351,672 B1 | 2/2002 | Park et al. |
| 6,366,813 B1 | 4/2002 | DiLorenzo |
| 6,416,471 B1 | 7/2002 | Kumar et al. |
| 6,433,690 B2 | 8/2002 | Petelenz et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,234 B1 | 10/2002 | Pyle |
| 6,466,821 B1 | 10/2002 | Pianca et al. |
| 6,468,234 B1 | 10/2002 | Van der Loos et al. |
| 6,473,639 B1 | 10/2002 | Fischell et al. |
| 6,514,218 B2 | 2/2003 | Yamamoto |
| 6,539,249 B1 | 6/2003 | Bonnet |
| 6,574,507 B1 | 6/2003 | Bonnet |
| 6,597,954 B1 | 7/2003 | Pless et al. |
| 6,605,038 B1 | 8/2003 | Teller et al. |
| 6,611,783 B2 | 8/2003 | Kelly, Jr. et al. |
| 6,626,902 B1 | 9/2003 | Kucharczyk et al. |
| 6,659,968 B1 | 12/2003 | McClure |
| 6,665,558 B2 | 12/2003 | Kalgren et al. |
| 6,687,538 B1 | 2/2004 | Hrdlicka et al. |
| 6,731,984 B2 | 5/2004 | Cho et al. |
| 6,735,474 B1 | 5/2004 | Loeb et al. |
| 6,752,766 B2 | 6/2004 | Kowallik et al. |
| 6,773,404 B2 | 8/2004 | Poezevera et al. |

(56) References Cited

U.S. PATENT DOCUMENTS

| | | |
|---|---|---|
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,937,891 B2 | 8/2005 | Leinders et al. |
| 6,941,171 B2 | 9/2005 | Mann et al. |
| 6,964,641 B2 | 11/2005 | Cho et al. |
| 6,993,380 B1 | 1/2006 | Modarres |
| 7,130,689 B1 | 10/2006 | Turcott |
| 7,141,026 B2 | 11/2006 | Aminian et al. |
| 7,141,034 B2 | 11/2006 | Eppstein et al. |
| 7,151,961 B1 | 12/2006 | Whitehurst et al. |
| 7,155,279 B2 | 12/2006 | Whitehurst et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,209,787 B2 | 4/2007 | DiLorenzo |
| 7,309,314 B2 | 12/2007 | Grant et al. |
| 7,313,440 B2 | 12/2007 | Miesel |
| 7,330,760 B2 | 2/2008 | Heruth et al. |
| 7,366,572 B2 | 4/2008 | Heruth et al. |
| 7,395,113 B2 | 7/2008 | Heruth et al. |
| 7,415,308 B2 | 8/2008 | Gerber et al. |
| 7,447,545 B2 | 11/2008 | Heruth et al. |
| 7,468,040 B2 | 12/2008 | Hartley et al. |
| 7,491,181 B2 | 2/2009 | Heruth et al. |
| 7,542,803 B2 | 6/2009 | Heruth et al. |
| 7,580,752 B2 | 8/2009 | Gerber et al. |
| 7,590,453 B2 | 9/2009 | Heruth et al. |
| 7,590,455 B2 | 9/2009 | Heruth et al. |
| 7,717,848 B2 | 5/2010 | Heruth et al. |
| 7,775,993 B2 | 8/2010 | Heruth et al. |
| 7,787,946 B2 | 8/2010 | Stahmann et al. |
| 7,792,583 B2 | 9/2010 | Miesel et al. |
| 7,805,196 B2 | 9/2010 | Miesel et al. |
| 7,853,322 B2 | 12/2010 | Bourget et al. |
| 7,860,561 B1 | 12/2010 | Modarres |
| 7,881,798 B2 | 2/2011 | Heruth et al. |
| 7,908,013 B2 | 3/2011 | Miesel et al. |
| 8,032,224 B2 | 10/2011 | Miesel et al. |
| 8,073,534 B2 | 12/2011 | Low |
| 8,190,253 B2 | 5/2012 | Heruth et al. |
| 8,244,340 B2 | 8/2012 | Wu et al. |
| 8,285,372 B2 | 10/2012 | Sing |
| 8,308,661 B2 | 11/2012 | Miesel et al. |
| 8,335,568 B2 | 12/2012 | Heruth et al. |
| 8,337,431 B2 | 12/2012 | Heruth et al. |
| 8,725,244 B2 | 5/2014 | Miesel et al. |
| 8,744,587 B2 | 6/2014 | Miesel et al. |
| 8,758,242 B2 | 6/2014 | Miesel et al. |
| 9,205,264 B2 | 12/2015 | Heruth et al. |
| 9,592,379 B2 | 3/2017 | Heruth et al. |
| 10,251,595 B2 | 4/2019 | Heruth et al. |
| 10,300,283 B2 | 5/2019 | Miesel et al. |
| 2001/0031930 A1 | 10/2001 | Roizen et al. |
| 2001/0037067 A1 | 11/2001 | Tchou et al. |
| 2001/0041831 A1 | 11/2001 | Starkweather et al. |
| 2001/0049471 A1 | 12/2001 | Suzuki et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0167485 A1 | 11/2002 | Hedrick |
| 2002/0169485 A1* | 11/2002 | Pless ............... A61B 5/0488 607/48 |
| 2002/0177882 A1 | 11/2002 | DiLorenzo |
| 2002/0177883 A1 | 11/2002 | Tziviskos et al. |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0055348 A1 | 3/2003 | Chazal et al. |
| 2003/0135917 A1 | 7/2003 | Ruane |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0195588 A1 | 10/2003 | Fischell et al. |
| 2003/0204219 A1 | 10/2003 | Gielen |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0077995 A1 | 4/2004 | Ferek-petric et al. |
| 2004/0088025 A1 | 5/2004 | Gesotti |
| 2004/0102814 A1 | 5/2004 | Sorenson et al. |
| 2004/0111040 A1 | 6/2004 | Ni et al. |
| 2004/0111041 A1 | 6/2004 | Ni et al. |
| 2004/0138719 A1 | 7/2004 | Cho et al. |
| 2004/0199214 A1 | 10/2004 | Merfeld et al. |
| 2004/0199217 A1 | 10/2004 | Lee et al. |
| 2004/0215269 A1 | 10/2004 | Burnes et al. |
| 2004/0220621 A1 | 11/2004 | Zhou et al. |
| 2005/0021103 A1 | 1/2005 | DiLorenzo |
| 2005/0021104 A1* | 1/2005 | DiLorenzo ......... A61N 1/36082 607/45 |
| 2005/0039745 A1 | 2/2005 | Stahmann et al. |
| 2005/0042589 A1 | 2/2005 | Hatlestad et al. |
| 2005/0043772 A1 | 2/2005 | Stahmann et al. |
| 2005/0060001 A1 | 3/2005 | Singhal et al. |
| 2005/0061320 A1 | 3/2005 | Lee et al. |
| 2005/0065560 A1 | 3/2005 | Lee et al. |
| 2005/0076908 A1 | 4/2005 | Lee et al. |
| 2005/0080463 A1 | 4/2005 | Stahmann et al. |
| 2005/0081847 A1 | 4/2005 | Lee et al. |
| 2005/0085738 A1 | 4/2005 | Stahmann et al. |
| 2005/0113710 A1 | 5/2005 | Stahmann et al. |
| 2005/0115561 A1 | 6/2005 | Stahmann et al. |
| 2005/0119703 A1 | 6/2005 | DiLorenzo |
| 2005/0143617 A1 | 6/2005 | Auphan |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222626 A1 | 10/2005 | DiLorenzo |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2005/0245988 A1 | 11/2005 | Miesel |
| 2006/0190049 A1 | 8/2006 | Gerber et al. |
| 2006/0224191 A1 | 10/2006 | DiLorenzo |
| 2006/0235472 A1 | 10/2006 | Geotz et al. |
| 2006/0293720 A1 | 12/2006 | DiLorenzo |
| 2007/0038265 A1 | 2/2007 | Tcheng et al. |
| 2007/0046408 A1 | 3/2007 | Shim |
| 2007/0049991 A1* | 3/2007 | Klostermann ...... A61N 1/37254 607/60 |
| 2007/0055324 A1* | 3/2007 | Thompson ......... A61N 1/37252 607/60 |
| 2007/0073355 A1 | 3/2007 | DiLorenzo |
| 2007/0142862 A1 | 6/2007 | DiLorenzo |
| 2007/0250134 A1 | 10/2007 | Miesel et al. |
| 2007/0255118 A1 | 11/2007 | Miesel et al. |
| 2007/0276439 A1 | 11/2007 | Miesel et al. |
| 2008/0125833 A1* | 5/2008 | Bradley ............... A61N 1/3605 607/60 |
| 2008/0154111 A1 | 6/2008 | Wu et al. |
| 2009/0030263 A1 | 1/2009 | Heruth et al. |
| 2009/0036951 A1 | 2/2009 | Heruth et al. |
| 2009/0082691 A1 | 3/2009 | Denison et al. |

(56) References Cited

U.S. PATENT DOCUMENTS

| | | | |
|---|---|---|---|
| 2009/0099627 A1 | 4/2009 | Molnar et al. | |
| 2010/0240945 A1* | 9/2010 | Bikko | A61B 5/7415 600/28 |
| 2013/0150921 A1 | 6/2013 | Singhal et al. | |
| 2013/0331906 A1 | 12/2013 | Krueger et al. | |
| 2016/0158552 A1 | 6/2016 | Heruth et al. | |
| 2016/0263382 A1 | 9/2016 | Heruth et al. | |
| 2017/0165481 A1 | 6/2017 | Menon | |

FOREIGN PATENT DOCUMENTS

| | | |
|---|---|---|
| EP | 0564803 A1 | 10/1993 |
| EP | 0849715 B1 | 6/1998 |
| EP | 1195139 A1 | 4/2002 |
| EP | 1291036 A2 | 3/2003 |
| EP | 1308182 A2 | 5/2003 |
| EP | 1437159 A1 | 7/2004 |
| EP | 1322227 B1 | 12/2005 |
| GB | 2330912 A | 5/1999 |
| WO | WO1998/000197 A1 | 1/1998 |
| WO | WO1999/013765 A1 | 3/1999 |
| WO | WO2001/037930 A1 | 5/2001 |
| WO | WO2002/028282 A1 | 4/2002 |
| WO | WO2002/041771 A1 | 5/2002 |
| WO | WO2002/087433 A1 | 11/2002 |
| WO | WO2002/0096512 A1 | 12/2002 |
| WO | WO2002/0100267 A1 | 12/2002 |
| WO | WO2003/024325 A2 | 3/2003 |
| WO | WO2003/051356 A1 | 6/2003 |
| WO | WO2003/065891 A2 | 8/2003 |
| WO | WO2005/028029 A2 | 3/2005 |
| WO | WO2005/035050 A1 | 4/2005 |

OTHER PUBLICATIONS

Amzica, "Physiology of Sleep and Wakefulness as it Relates to the Physiology of Epilepsy," Journal of Clinical Neurophysiology, American Clinical Neurophysiology Society, 19(6), Dec. 2002, pp. 488-503.
"Analysis of heart rate dynamics by methods derived from nonlinear mathematics: Clinical applicability and prognostic significance," http://herkules.oulu.fi.isbn9514250133/html, Oct. 2004, 4 pp.
Antonini et al., "Deep brain stimulation and its effect on sleep in Parkinson's disease," Sleep Medicine, vol. 5, Issue 2, Mar. 2004, pp. 211-214.
"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.
"Bitestrip Flier," downloaded from Internet Archive of www.quietsleep.com dated Jan. 29, 2005, http://web.archive.org/web/20041124080003/www.quietsleep.com/pdf/bitestrip+Flier.pdf., 1 pp.
Cicolin et al., "Effects of deep brain stimulation of the subthalamic nucleus on sleep architecture in parkinsonian patients," Sleep Medicine, vol. 5, Issue 2, Mar. 2004, pp. 207-210.
Criticare System Inc., -504DX Portable Pulse Oximeter, http://www.csiusa.com/504dx.html, 4 pgs. Jan. 31, 2005.
"Design Competition: Runners-Up for the Best Three Designs," EPN, vol. 26, No. 1, 1 pg., (2002). "Watch," Wikipedia, the free encyclopedia, 6 pgs., http://en.wikipedia.org/wiki/Watch (Applicant points out, in accordance with MPEP 609.04(a), that the year of publication, 2002, is sufficiently earlier than the effective U.S. filing date, so that the particular month of publication is not in issue.).
Dinner, "Effect of Sleep of Epilepsy," Journal of Clinical Neurophysiology, American Clinical Neurophysiology Society, 19(6), Dec. 2002, pp. 504-513.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, Dec. 2002.
Gennaro et al., "Sleep spindles: an overview," Sleep Medicine Reviews, vol. 7, No. 5, pp. 423-440, Oct. 2003.
Goodrich et al., "The Prediction of Pain Using Measures of Sleep Quality," Pain Digest, 8:23-25, (1998) (Applicant points out, in accordance with MPEP 609.04(a), that the year of publication, 1998, is sufficiently earlier than the effective U.S. filing date, so that the particular month of publication is not in issue.).
Greenberg et al., "Mechanisms and the Current State of Deep Brain Stimulation in Neuropsychiatry," CNC Spectrums, vol. 8, No. 7, pp. 522-526, Jul. 2003.
Hadas et al., "The BiteStrip: A Novel Screener for Sleep Bruxism," Journal of Sleep and Sleep Disorders Research, vol. 24, Apr. 15, 2001, 1 pp.
"IBM & Citizen Watch develop Linux-based WatchPad," 5 pgs., http://www.linuxdevices.com/news/NS6580187845.html, Feb. 20, 2006.
"Merlin—The complex for ambulatory apnoe-diagnostics," accessed from http://www.aha.ru/~pir/english/merlin/, accessed on May 29, 2019, 3 pp.
"MiniMitter Physiological and Behavioral Monitoring for Humans and Animals," http://www.minimitter.com/Products/Actiwatch, 3 pgs., Feb. 20, 2006.
"Watch," Wikipedia, the free encyclopedia, 6 pgs., http://en.wikipedia.org/wiki/Watch, Feb. 20, 2006.
Itamar Medical Information, http://itamar-medical.com/content.asp?id=31, 2 pgs. Jan. 31, 2005.
Kassam, "2005 EDP Topic 'MK4': Tremor Data-Logger for Parkinson's Disease Patients," http://www.ee.rverson.ca/-courses/edo2005/MK4.html, 3 pgs., Feb. 20, 2006.
Kerr et al., "Analysis of the sit-stand-sit movement cycle in normal subjects," Clinical Bimechanics, vol. 12, No. 4, Jun. 1997, pp. 236-245.
Macarthur et al., "Sleep quality and endocrine markers of sleep quality," Last revised Sep. 1997, http://www.macses.ucsf.edu/ResearchAllostatic/notebook/sleep.html, archived page dated Feb. 10, 2001 acccessed through http://web.archive.org on Oct. 2, 2007.
MAP Medizin-Technologie GmbH, Poly-MESAM, http://195.244.124.130/map/de/eng/map_med.nsf/cmsall/70564A3FCBE4188AC1256EF4.., 4 pgs. Jan. 31, 2005.
Medicare—A Global Leader in Sleep Diagnostics, Embletta Recording System, http://www.medcare.com/products/diagnostic/embletta/, 2 pgs. Jan. 31, 2005.
Mendez et at. "Interactions Between Sleep and Epilepsy," Journal of Clinical Neurophysiology, American Clinical Neurophysiology Society, 18 (2), pp. 106-127, Mar. 2001.
Oerlemans et al., "The prevalence of sleep disorders in patients with Parkinson's disease. A self-reported, community-based survey," Sleep Medicine, vol. 3, Issue 2, pp. 147-149, Mar. 2002.
Rechtschaffen et al., A manual of standardized terminology, techniques and scoring system for sleep stages of human subjects, Public Health Service, U.S. Government Printing Office, 1968 (reprinted 1971). (Applicant points out, in accordance with MPEP 609.04(a), that the year of publication, 1971, is sufficiently earlier than the effective U.S. filing date, so that the particular month of publication is not in issue.).
Ricci et al., "Transient effects of 80 Hz stimulation on gait in STN DBS treated PD patients: A 15 months follow-up study," Brain Stimulation, vol. 5, No. 3, Jul. 1, 2012, 5 pp.
Singh et ai.,"Freezing of Gait-Related Oscillatory Activity in the Human Subthalamic Nucleus," Basal Ganglia, vol. 3, No. 1, Mar. 1, 2013, pp. 25-32.
Sleep Solutions—PR Newswire: Sleep Solutions Introduces NovaSom QSG for PSG., http://www.sleep-solutions.com/press_room/novasom.htm, 2 pgs. Jan. 31, 2005.
Sleep Strip & Bite Strip, http://www.quietsleep.com/snoringapnea/sleepstrip.htm, 7 pgs. Jan. 31, 2005.
Smith et al. "How do sleep disturbance and chronic pain interrelate? Insights from the longitudinal and cognitive-behavioral clinical trials literature," Sleep Medicine Reviews, YSMRV 286, pp. 1-14, (2003) (Applicant points out, in accordance with MPEP

(56) References Cited

OTHER PUBLICATIONS 609.04(a), that the year of publication, 2003, is sufficiently earlier than the effective U.S. filing date, so that the particular month of publication is not in issue.).

Smith et al., "Presleep Cognitions in Patients with Insomnia Secondary to Chronic Pain," Journal of Behavioral Medicine, vol. 24, No. 1, pp. 93-114, Feb. 2001.

Snap® Laboratories, Product Fact Sheet, http://www.snaplab.com/mp_fact.htm, 2 pp. Jan. 31, 2005.

Toledo et al., "High beta activity in the subthalamic nucleus and freezing of gait in Parkinson's disease," Neurobiology of Disease, vol. 64, Jan. 1, 2014, 6 pp.

Tuisku, "Motor Activity Measured by Actometry in Neuropsychiatric Disorders," Department of Psychiatry, University of Helsinki, Helsinki, Finland, Dec. 13, 2002, 115 pp.

Van Dam et al., "Measuring physical activity in patients after surgery for a malignant tumour in the leg," The Journal of Bone & Joint Surgery, vol. 83-B, No. 7, Sep. 2001, pp. 1015-1019.

Prosecution History from U.S. Appl. No. 11/591,286, dated Oct. 27, 2011 through Dec. 23, 2013, 300 pp.
Prosecution History from U.S. Appl. No. 14/247,923, dated May 23, 2016 through Apr. 22, 2019, 247 pp.
Prosecution History from U.S. Appl. No. 10/826,925, dated Mar. 16, 2007 through Dec. 16, 2009, 132 pp.
Prosecution History from U.S. Appl. No. 11/081,811, dated Mar. 25, 2008 through Jan. 19, 2016, 443 pp.
Prosecution History from U.S. Appl. No. 11/691,376, dated Nov. 9, 2011 through Jul. 17, 2012, 122 pp.
Prosecution History from U.S. Appl. No. 12/723,501, dated Nov. 5, 2012 through May 28, 2014, 78 pp.
Prosecution History from U.S. Appl. No. 14/276,516, dated Feb. 25, 2015 through Aug. 5, 2015, 48 pp.
Prosecution History from U.S. Appl. No. 14/961,344, dated Mar. 24, 2016 through Dec. 7, 2016, 36 pp.
Prosecution History from U.S. Appl. No. 15/160,455, dated Mar. 7, 2019 through Nov. 27, 2019, 106 pp.

* cited by examiner

| PARAMETER SET | PARAMETERS | SLEEP EFFICIENCY | SLEEP LATENCY | DEEP SLEEP |
| --- | --- | --- | --- | --- |
| 1 | PA = 5.5V<br>PW = 210ms<br>PR = 90Hz | 85% | 20 min. | 4 hours |
| 2 | PA = 5V<br>PW = 190ms<br>PR = 95Hz | 75% | 25 min. | 3.8 hours |
| ••• | | | | |
| N | PA = 4.6V<br>PW = 215ms<br>PR = 80Hz | 70% | 38 min. | 3.0 hours |

DETERMINATION OF SLEEP QUALITY FOR NEUROLOGICAL DISORDERS

This application is a divisional of U.S. application Ser. No. 14/247,923, filed Apr. 8, 2014, which is a continuation of U.S. application Ser. No. 11/591,286, filed Oct. 31, 2006 and issued as U.S. Pat. No. 8,725,244, which claims the benefit of U.S. Provisional Application No. 60/785,678, filed Mar. 24, 2006 and is a continuation-in-part of U.S. application Ser. No. 11/081,811, filed Mar. 16, 2005, which is a continuation-in-part of U.S. application Ser. No. 10/826,925, filed Apr. 15, 2004 and issued as U.S. Pat. No. 7,717,848, which claims the benefit of U.S. Provisional Application No. 60/553,783, filed Mar. 16, 2004. The entire content of each of these applications is incorporated herein by reference.

TECHNICAL FIELD

The invention relates to medical devices and, more particularly, to medical devices that monitor physiological parameters.

BACKGROUND

In some cases, an ailment may affect the quality of a patient's sleep. For example, neurological disorders may cause a patient to have difficulty falling asleep, and may disturb the patient's sleep, e.g., cause the patient to wake. Further, neurological disorders may cause the patient to have difficulty achieving deeper sleep states, such as one or more of the nonrapid eye movement (NREM) sleep states.

Epilepsy is an example of a neurological disorder that may affect sleep quality. In some patients, epileptic seizures may be triggered by sleep or transitions between the sleep states, and may occur more frequently during sleep. Furthermore, the occurrence of seizures may disturb sleep, e.g., wake the patient. Often, epilepsy patients are unaware of the seizures that occur while they sleep, and suffer from the effects of disturbed sleep, such as daytime fatigue and concentration problems, without ever knowing why.

Other neurological disorders that may negatively affect patient sleep quality include movement disorders, such as tremor, Parkinson's disease, multiple sclerosis, or spasticity. The uncontrolled movements associated with such movement disorders may cause a patient to have difficulty falling asleep, disturb the patient's sleep, or cause the patient to have difficulty achieving deeper sleep states. Psychological disorders, such as depression, mania, bipolar disorder, or obsessive-compulsive disorder, may also similarly affect the ability of a patient to sleep, or at least experience quality sleep. In the case of depression, a patient may "sleep" for long periods of the day, but the sleep is not restful, e.g., includes excessive disturbances and does not include deeper, more restful sleep states. Further, chronic pain, whether of neurological origin or not, as well as congestive heart failure, gastrointestinal disorders and incontinence, may disturb sleep or otherwise affect sleep quality.

Further, in some cases, poor sleep quality may increase the symptoms experienced by a patient due to a neurological disorder. For example, poor sleep quality has been linked to increased pain symptoms in chronic pain patients and increased seizure activity in epileptic patients, and may also result in increased movement disorder symptoms in movement disorder patients. Further, poor sleep quality may exacerbate many psychological disorders, such as depression. The link between poor sleep quality and increased symptoms is not limited to ailments that negatively impact sleep quality, such as those listed above. Nonetheless, the condition of a patient with such an ailment may progressively worsen when symptoms disturb sleep quality, which in turn increases the frequency and/or intensity of symptoms.

SUMMARY

In general, the invention is directed to techniques for collecting information that relates to the quality of patient sleep via a medical device, such as an implantable medical device (IMD). In particular, values for one or more metrics that indicate the quality of the patient's sleep are determined based on at least one sensed physiological parameter signal. In some embodiments, sleep quality information is presented to a user based on the sleep quality metric values. A clinician, for example, may use the presented sleep quality information to evaluate the effectiveness of therapy delivered to the patient by the medical device, to adjust the therapy delivered by the medical device, or to prescribe a therapy not delivered by the medical device in order to improve the quality of the patient's sleep.

In some embodiments, the medical device may deliver the therapy to treat a non-respiratory neurological disorder, such as epilepsy, a movement disorder, or a psychological disorder. As discussed above, examples of movement disorders are tremor, Parkinson's disease, multiple sclerosis, or spasticity, and examples of psychological disorders are depression, mania, bipolar disorder, or obsessive-compulsive disorder. The medical device may be implanted or external, and may deliver, for example, electrical stimulation, a therapeutic agent, such as a drug, and/or a thermal, e.g., cooling, therapy. In some embodiments, the medical device may deliver deep brain stimulation (DBS) therapy to treat a non-respiratory neurological disorder, or other disorder or symptom, and may by implanted on or recessed into the cranium beneath the scalp.

The medical device that delivers the therapy or a separate monitoring device monitors one or more physiological parameter signals. Example physiological parameters include activity level, posture, heart rate, electrocardiogram (ECG) morphology, electroencephalogram (EEG) morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, melatonin level within one or more bodily fluids, brain electrical activity, eye motion, and galvanic skin response. In order to monitor one or more of these parameters, the medical device or monitoring device may include, or be coupled to one or more sensors, each of which generates a signal as a function of one or more of these physiological parameters.

The medical device or monitoring device may determine a value of one or more sleep quality metrics based on the one or more monitored physiological parameters, and/or the variability of one or more of the monitored physiological parameters. In other embodiments, one or both of the medical device or monitoring device records values of the one or more physiological parameters, and provides the physiological parameter values to a programming device, such as a clinician programming device or a patient programming device, or another computing device. In such embodiments, the programming or other computing device determines values of one or more sleep quality metrics based on the physiological parameter values received from the medical device and/or the variability of one or more of the physiological parameters. The medical device or monitoring device may provide the recorded physiological parameter values to the programming or other computing device in real time, or may provide physiological parameter values recorded over a period of time to the programming or other computing device when interrogated.

Sleep efficiency and sleep latency are example sleep quality metrics for which a medical device or programming device may determine values. Sleep efficiency may be measured as the percentage of time while the patient is attempting to sleep that the patient is actually asleep. Sleep latency may be measured as the amount of time between a first time when the patient begins attempting to fall asleep and a second time when the patient falls asleep, and thereby indicates how long a patient requires to fall asleep.

The time when the patient begins attempting to fall asleep may be determined in a variety of ways. For example, the patient may provide an indication that he or she is trying to fall asleep, e.g., via a patient programming device. In other embodiments, the medical device or monitoring device may monitor the activity level of the patient, and the time when the patient is attempting to fall asleep may be identified by determining whether the patient has remained inactive for a threshold period of time, and identifying the time at which the patient became inactive. In still other embodiments, the medical device or monitoring device may monitor patient posture, and the medical device or a programming device may identify the time when the patient is recumbent, e.g., lying down, as the time when the patient is attempting to fall asleep. In these embodiments, the medical device or monitoring device may also monitor patient activity, and either the medical device, monitoring device, programming device, or other computing device may confirm that the patient is attempting to sleep based on the patient's activity level.

As another example, the medical device or monitoring device may determine the time at which the patient begins attempting to fall asleep based on the level of melatonin within one or more bodily fluids, such as the patient's blood, cerebrospinal fluid (CSF), or interstitial fluid. The medical device or monitoring device may also determine a melatonin level based on metabolites of melatonin located in the saliva or urine of the patient. Melatonin is a hormone secreted by the pineal gland into the bloodstream and the CSF as a function of exposure of the optic nerve to light, which synchronizes the patient's circadian rhythm. In particular, increased levels of melatonin during evening hours may cause physiological changes in the patient, which, in turn, may cause the patient to attempt to fall asleep. The medical device or monitoring device may, for example, detect an increase in the level of melatonin, and estimate the time that the patient will attempt to fall asleep based on the detection.

The time at which the patient has fallen asleep may be determined based on the activity level of the patient and/or one or more of the other physiological parameters that may be monitored by the medical device as indicated above. For example, a discernable change, e.g., a decrease, in one or more physiological parameters, or the variability of one or more physiological parameters, may indicate that the patient has fallen asleep. A decrease in respiration rate or respiration rate variability, or heart rate or heart rate variability, as examples, may indicate that a patient is asleep.

In some embodiments, a sleep probability metric value may be determined based on a value of a physiological parameter monitored by the medical device. In such embodiments, the sleep probability metric value may be compared to a threshold to identify when the patient has fallen asleep. In some embodiments, a plurality of sleep probability metric values are determined based on a value of each of a plurality of physiological parameters, the sleep probability values are averaged or otherwise combined to provide an overall sleep probability metric value, and the overall sleep probability metric value is compared to a threshold to identify the time that the patient falls asleep.

Thus, in some embodiments, whether a patient is sleeping may be determined based on a statistical combination of two or more physiological parameters. For example, whether a patient is sleeping may be determined based on a statistical combination of at least one of activity level or posture, with at least one of brain electrical activity or EEG morphology, and also with core temperatures. Other combinations of the physiological parameters described herein are contemplated. A sleep probability metric value may be determined for each of the physiological parameters based on a current value of the parameter, e.g., by application of an equation or look-up table to the value. The sleep probability metric values may be combined, e.g., by average or sum, which may be weighted, in order to determine whether the patient is asleep based on the plurality of physiological parameters.

Other sleep quality metrics that may be determined include total time sleeping per day, the amount or percentage of time sleeping during nighttime or daytime hours per day, and the number of apnea and/or arousal events per night. In some embodiments, which sleep state the patient is in, e.g., rapid eye movement (REM), or one of the nonrapid eye movement (NREM) states (S1, S2, S3, S4) may be determined based on physiological parameters monitored by the medical device, such as the EEG signal. The amount of time per day spent in these various sleep states may also be a sleep quality metric. Because they provide the most "refreshing" type of sleep, the amount of time spent in one or both of the S3 and S4 sleep states, in particular, may be determined as a sleep quality metric. In some embodiments, average or median values of one or more sleep quality metrics over greater periods of time, e.g., a week or a month, may be determined as the value of the sleep quality metric. Further, in embodiments in which values for a plurality of the sleep quality metrics are determined, a value for an overall sleep quality metric may be determined based on the values for the plurality of individual sleep quality metrics.

As discussed above, in some embodiments, the medical device delivers a therapy. At any given time, the medical device delivers the therapy according to a current set of therapy parameters. For example, in embodiments in which the medical device delivers electrical stimulation, a therapy parameter set may include a pulse amplitude, a pulse width, a pulse rate, a duty cycle, and an indication of active electrodes. Different therapy parameter sets may be selected, e.g., by the patient via a programming device or the medical device according to a schedule, and parameters of one or more therapy parameter sets may be adjusted by the patient to create new therapy parameter sets. In other words, over time, the medical device delivers the therapy according to a plurality of therapy parameter sets.

In embodiments in which the medical device determines sleep quality metric values, the medical device may identify the current therapy parameter set that was in use when a value of one or more sleep quality metrics is collected, and may associate that value with the therapy parameter set. For each available therapy parameter set the medical device may store a representative value of each of one or more sleep quality metrics in a memory with an indication of the therapy programs with which that representative value is associated. A representative value of sleep quality metric for a therapy parameter set may be the mean or median of collected sleep quality metric values that have been associated with that therapy parameter set. In other embodiments in which a programming device or other computing device determines sleep quality metric values, the medical device may associate recorded physiological parameter values with the current therapy parameter set in the memory.

Further, in embodiments in which a separate monitoring device records physiological parameter values or determines sleep quality metric values, the monitoring device may mark recorded physiological parameter values or sleep quality metric values with a current time in a memory, and the medical device may store an indication of a current therapy parameter set and time in a memory. A programming device or other computing device may receive indications of the physiological parameter values or sleep quality metrics and associated times from the monitoring device, and indications of the therapy parameter sets and associated times from the medical device, and may associate the physiological parameter values or sleep quality metrics with the therapy parameter set that was delivered by the medical device when the physiological parameter values or sleep quality metrics were collected.

A programming device or other computing device according to the invention may be capable of wireless communication with the medical device, and may receive sleep quality metric values or recorded physiological parameter values from the medical device or a separate monitoring device. In either case, when the computing device either receives or determines sleep quality metric values, the computing device may provide sleep quality information to a user based on the sleep quality metric values. For example, the computing device may be a patient programmer, and may provide a message to the patient related to sleep quality. The patient programmer may, for example, suggest that the patient visit a clinician for prescription of sleep medication or for an adjustment to the therapy delivered by the medical device. As other examples, the patient programmer may suggest that the patient increase the intensity of therapy delivered by the medical device during nighttime hours relative to previous nights, or select a different therapy parameter set for use during sleep than the patient had selected during previous nights. Further, the patient programmer may provide a message that indicates the quality of sleep to the patient to, for example, provide the patient with an objective indication of whether his or her sleep quality is good, adequate, or poor.

In other embodiments, the computing device is a clinician programmer that presents information relating to the quality of the patient's sleep to a clinician. The clinician programmer may present, for example, a trend diagram of values of one or more sleep quality metrics over time. As other examples, the clinician programmer may present a histogram or pie chart illustrating percentages of time that a sleep quality metric was within various value ranges.

As indicated above, the computing device may receive representative values for one or more sleep quality metrics or the physiological parameter values from the therapy delivering medical device or separate monitoring device. The computing device may receive information identifying the therapy parameter set with which the representative values are associated, or may itself associate received physiological parameter or sleep quality metric values with therapy parameter sets based on time information received from one or more devices. In embodiments in which the computing device receives physiological parameter values, the computing device may determine sleep quality metric values associated with the plurality of parameter sets based on the physiological parameter values, and representative sleep quality metric values for each of the therapy parameter sets based on the sleep quality metric values associated with the therapy parameter sets. In some embodiments, the computing device may determine the variability of one or more of the physiological parameters based on the physiological parameter values received from the medical device or monitoring device, and may determine sleep quality metric values based on the physiological parameter variabilities.

The computing device may display a list of the therapy parameter sets to the clinician ordered according to their associated representative sleep quality metric values. Such a list may be used by the clinician to identify effective or ineffective therapy parameter sets. Where a plurality of sleep quality metric values are determined, the programming device may order the list according to values of a user-selected one of the sleep quality metrics.

In other embodiments, a system according to the invention does not include a programming or other computing device. For example, an external medical device according to the invention may include a display, determine sleep quality metric values, and display sleep quality information to a user via the display based on the sleep quality metric values. Further, any of the devices described herein may automatically select or adjust a therapy parameter set based on sleep quality metric values, e.g., select one of a plurality of therapy parameter sets based on the representative sleep quality metric values associated with each of the plurality of therapy parameter sets.

In one embodiment, the invention is directed to a method comprising delivering a therapy from a medical device to a patient to treat a non-respiratory neurological disorder of the patient, sensing at least one physiological parameter signal during treatment of the patient with the medical device, determining values of a sleep quality metric based on the at least one physiological parameter signal, and providing the sleep quality metric values to a user for evaluation of the therapy.

In another embodiment, the invention is directed to a medical system comprising a medical device that delivers a therapy to a patient to treat a non-respiratory neurological disorder of the patient, and a processor that determines values of a sleep quality metric based on at least one physiological parameter signal sensed during treatment of the patient with the medical device, and provides the sleep quality metric values to a user for evaluation of the therapy.

In another embodiment, the invention is directed to a method comprising delivering deep brain stimulation (DBS) therapy from a medical device to a patient via a lead implanted in a brain of the patient, sensing at least one physiological parameter signal during treatment of the patient with the medical device, determining values of a sleep quality metric based on the at least one physiological parameter signal, and providing the sleep quality metric values to a user for evaluation of the DBS therapy.

In another embodiment, the invention is directed to a medical system comprising a lead implanted in a brain of a patient, a medical device coupled to the lead that delivers deep brain stimulation (DBS) therapy to the patient via the lead, and a processor that determines values of a sleep quality metric based on at least one physiological parameter signal sensed during treatment of the patient with the medical device, and provides the sleep quality metric values to a user for evaluation of the DBS therapy.

The invention may be capable of providing one or more advantages. For example, by providing information related to the quality of a patient's sleep to a clinician and/or the patient, a system according to the invention can improve the course of treatment of a neurological disorder of the patient, such as chronic pain, epileptic seizures, a movement disorder, or a psychological disorder. Using the sleep quality information provided by the system, the clinician and/or patient can, for example, make changes to the therapy provided by a medical device in order to better address symptoms which are disturbing the patient's sleep. Further, a clinician may choose to prescribe a therapy that will improve the patient's sleep, such as a sleep inducing medication, in situations where poor sleep quality is increasing symptoms experienced by the patient. In addition, the system may detect which sleep state the patient is experiencing based upon the EEG signal.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 13 illustrates an example list of therapy parameter sets and associated sleep quality information that may be presented by a clinician programmer.

DETAILED DESCRIPTION

One or more physiological parameters are monitored to identify the quality of a patient's sleep. Some physiological parameters that may be monitored include activity, posture, heart rate, respiration rate, electrocardiogram (ECG) morphology, subcutaneous or core temperature, muscular tone, electrical activity of a brain of the patient, electroencephalogram (EEG) morphology, or eye motion. In some embodiments, for example, the EEG may be analyzed to detect if the patient is in the S1, S2, S3, S4, or REM sleep state. This sleep state information may be used to determine the duration of deep sleep for the patient, which may be indicative of the sleep quality of the patient. However, other physiological parameters such as activity, posture, core or subcutaneous temperature, or heart rate may be used instead of or in addition to the EEG when determining whether the patient is asleep, in which sleep state the patient is, or the quality of sleep for the patient in general.

Sleep quality information may take the form of values for one or more sleep quality metrics. A person or device may evaluate or modify a therapy based on sleep quality metric values in an effort to improve therapy efficacy. In some embodiments, sleep quality metric values may be associated with the current therapy parameter set that is being used to deliver the therapy, and the effectiveness of each of a plurality of therapy parameter sets may be evaluated by reviewing their associated sleep quality metric values. In some embodiments, an implanted medical device (IMD) may deliver therapy, monitor the one or more physiological parameters, determine associated sleep quality metric values, and, in some cases, make changes to the therapy based upon the sleep quality metric values. Systems according to the invention may help to improve therapy effectiveness and overall patient quality of life.

Figure 1:
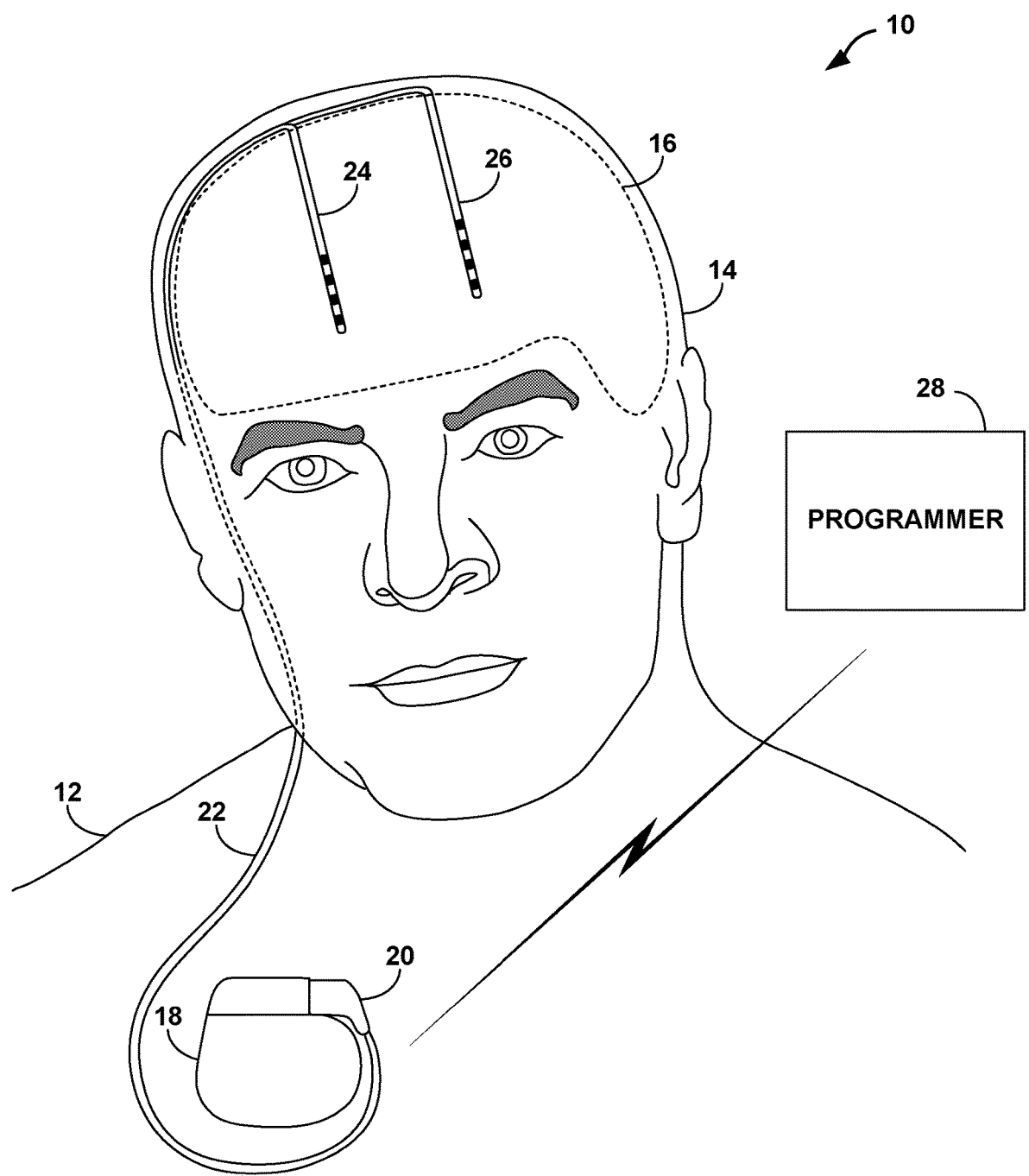
FIG. 1 is a conceptual diagram illustrating an example system that includes an implantable medical device implanted in the chest that collects sleep quality information.

FIG. 1 is a conceptual diagram illustrating an example system 10 that includes an implantable medical device (IMD) 18 implanted in the chest of a patient 12. IMD 18 collects information relating to the quality of sleep experienced by patient 12. Sleep quality information collected by IMD 18 may be provided to a user, such as a clinician or the patient. Using the sleep quality information collected by IMD 18, a current course of therapy for an ailment of patient 12 may be evaluated, and an improved course of therapy for the ailment may be identified. In some embodiments, IMD 18 automatically processes the sleep quality information and autonomously modifies the therapy in an attempt to improve sleep quality.

In the illustrated example, IMD 18 takes the form of an implantable neurostimulator that delivers neurostimulation therapy in the form of electrical pulses to patient 12. However, the invention is not limited to implementation via an implantable neurostimulator. For example, in some embodiments of the invention, an implantable pump that delivers a drug or other therapeutic agent to brain, intrathecal space, or other locations within patient may collect sleep quality information. In the case of a drug delivery device, a therapy parameter set may determine the flow rate of delivery and delivery timing for a fluid drug. As another example, the invention may be embodied in a device that delivers a thermal therapy, e.g., cooling therapy, to the brain or other tissues instead of or in addition to electrical stimulation or a therapeutic agent. In other embodiments, an implantable cardiac rhythm management device, such as a pacemaker, may collect sleep quality information.

Further, the invention is not limited to implementation via an IMD, and a device that collects sleep quality information need not deliver a therapy. In some cases, a system may include a therapy delivering device, and a monitor that collects sleep quality information. In other words, any implantable or external medical device, which does or does not deliver therapy, may collect sleep quality information according to the invention.

In the example of FIG. 1, IMD 18 delivers neurostimulation therapy to patient 12 via leads 24 and 26, which are connected to IMD 18 via a lead extension 22. Lead extension 22 couples to IMD 18 via connector 20. Leads 24 and 26 may, as shown in FIG. 1, be implanted within the cerebrum of the brain of patient 12, and IMD 18 may deliver stimulation therapy to the brain, e.g., deep brain stimulation (DBS). In the illustrated example, leads 24 and 26 are symmetrical or stereotactic, i.e., both leads are implanted at similar locations in each the right and left hemisphere of brain 16. In this manner, IMD 18 delivers stimulation to bilateral locations within brain 16.

However, the invention is not limited to the configuration of leads 24 and 26 or extensions 22 shown in FIG. 1. In other embodiments, non-symmetrical leads or a single lead may be used to deliver DBS therapy. In other words, one or more leads 24 and 26 may be coupled directly to IMD 18, or be coupled to IMD 18 by one or more extensions 22, and may extend from IMD 18 to any one or more portions of brain 16.

IMD 18 may deliver electrical stimulation to the brain to treat any of a variety of neurological disorders. For example, IMD 18 may deliver DBS in order to, for example, reduce the frequency and severity of epileptic seizures experienced by patient 12. As other examples, IMD 18 may deliver DBS in order to reduce the symptoms of a movement disorder or psychological disorder, such as tremor, Parkinson's disease, multiple sclerosis, spasticity, depression, mania, bipolar disorder, or obsessive-compulsive disorder. Additionally, IMD 18 may deliver DBS to treat chronic pain or other non-respiratory neurological disorders, e.g., excluding for example central sleep apnea. Further, IMD 18 may deliver stimulation to locations other than the brain to treat such disorders, or may deliver stimulation to the brain to treat other disorders.

Additionally, leads 24 and 26 may be implanted proximate to the spinal cord to treat, for example, chronic pain; on or within the heart to treat any of a variety of cardiac disorders, such as congestive heart failure or arrhythmia; proximate to the gastrointestinal tract to treat any of a variety of gastrointestinal disorders, such as gastroparesis or constipation; within the pelvic floor to treat disorders such as incontinence; or proximate to any peripheral nerves to treat any of a variety of disorders, such as peripheral neuropathy or other types of chronic pain. IMD 18 may deliver either or both of responsive, e.g., closed-loop, or non-responsive stimulation. An example of responsive stimulation is delivery of DBS in response to detection of electrical activity within the brain of patient 12 associated with a seizure.

IMD 18 delivers therapy according to a set of therapy parameters, i.e., a set of values for a number of parameters that define the therapy delivered according to that therapy parameter set. In embodiments where IMD 18 delivers neurostimulation therapy in the form of electrical pulses, the parameters in each parameter set may include voltage or current pulse amplitudes, pulse widths, pulse rates, and the like. Further, each of leads 24 and 26 includes electrodes disposed at the distal end of each lead, and a therapy parameter set may include information identifying which electrodes have been selected for delivery of pulses, and the polarities of the selected electrodes. Therapy parameter sets used by IMD 18 may include parameter sets programmed by a clinician (not shown), and parameter sets representing adjustments made by patient 12 to these preprogrammed sets. In some embodiments, adjustments or modifications to therapy parameter sets may be performed automatically or suggested to patient 12 by IMD 18 or other components of system 10, such as a programmer.

In the illustrated example, system 10 includes a programmer 28. Programmer 28 may be a clinician or patient programmer that communicates with IMD 18, and system 10 may include any number of programmers 28 which may act as clinician or patient programmers. A clinician (not shown) may use programmer 28 to program therapy for patient 12, e.g., specify a number of therapy parameter sets and communicate the parameter sets to IMD 18. The clinician may also use programmer 28 to retrieve information collected by IMD 18. The clinician may use programmer 28 to communicate with IMD 18 both during initial programming of IMD 18, and for collection of information and further programming during follow-up visits.

Programmer 28 may include a display (not shown) to present information to the user and an input mechanism (not shown), e.g., a keypad, that allows the user to interact with the programmer. In some embodiments, the display may be a touch screen display, and a user may interact with programmer 28 via the display. A user may also interact with clinician programmer 28 using peripheral pointing devices, such as a stylus or mouse. The keypad may take the form of an alphanumeric keypad or a reduced set of keys associated with particular functions. Programmer 28 may be embodied similar to clinician programmer 128 or patient programmer 134 of FIG. 5. However, programmer 28 is not limited to the embodiments depicted in FIG. 5.

As described above, programmer 28 may be a patient programmer. Patient 12 may use programmer 28 to control the delivery of therapy by IMD 18. For example, using programmer 28, patient 12 may select a current therapy parameter set from among the therapy parameter sets preprogrammed by the clinician, or may adjust one or more parameters of a preprogrammed therapy parameter set to arrive at the current therapy parameter set.

Programmer 28 may be any type of computing device. For example, programmer 28 may be a hand-held or tablet-based computing device, a desktop computing device, or a workstation. In addition, programmer 28 may be a virtual programmer in that a remote user may communicate with IMD 18 without being in the same room as patient 12.

IMD 18 and programmer 28 communicate via wireless communication. Programmer 28 may communicate via wireless communication with IMD 18 using radio frequency (RF) telemetry techniques known in the art. Possible communications may follow RF protocols according to the 802.11 or Bluetooth specification sets, infrared communication according to the IRDA specification set, or other standard or proprietary telemetry protocols.

As mentioned above, IMD 18 collects information relating to the quality of sleep experienced by patient 12. Specifically, as will be described in greater detail below, IMD 18 monitors one or more physiological parameters of patient 12, and determines values for one or more metrics that indicate the quality of sleep based on values of the physiological parameters. Example physiological parameters that IMD 18 may monitor include activity level, posture, heart rate, ECG morphology, respiration rate, respiratory volume, blood pressure, blood oxygen saturation, partial pressure of oxygen within blood, partial pressure of oxygen within cerebrospinal fluid (CSF), muscular activity and tone, core temperature, subcutaneous temperature, arterial blood flow, the level of melatonin within one or more bodily fluids, brain electrical activity, electroencephalogram (EEG) morphology, and eye motion. In some external medical device embodiments of the invention, galvanic skin response may additionally or alternatively be monitored. Further, in some embodiments, IMD 18 additionally or alternatively monitors the variability of one or more of these parameters. In order to monitor one or more of these parameters, IMD 18 may include or be coupled to one or more sensors (not shown in FIG. 1), each of which generates a signal as a function of one or more of these physiological parameters.

For example, IMD 18 may determine sleep efficiency and/or sleep latency values. Sleep efficiency and sleep latency are example sleep quality metrics. IMD 18 may measure sleep efficiency as the percentage of time while patient 12 is attempting to sleep that patient 12 is actually asleep. IMD 18 may measure sleep latency as the amount of time between a first time when patient 12 begins attempting to fall asleep and a second time when patient 12 falls asleep.

IMD 18 may identify the time at which patient 12 begins attempting to fall asleep in a variety of ways. For example, IMD 18 may receive an indication from the patient that the patient is trying to fall asleep via programmer 28. In other embodiments, IMD 18 may monitor the activity level of patient 12, and identify the time when patient 12 is attempting to fall asleep by determining whether patient 12 has remained inactive for a threshold period of time, and identifying the time at which patient 12 became inactive. In still other embodiments, IMD 18 may monitor the posture of patient 12, and may identify the time when the patient 12 becomes recumbent, e.g., lies down, as the time when patient 12 is attempting to fall asleep. In these embodiments, IMD 18 may also monitor the activity level of patient 12, and confirm that patient 12 is attempting to sleep based on the activity level.

As another example, IMD 18 may determine the time at which patient 12 is attempting to fall asleep based on the level of melatonin within one or more bodily fluids of patient 12, such as the patient's blood, cerebrospinal fluid (CSF), or interstitial fluid. IMD 18 may also determine a melatonin level based on metabolites of melatonin located in the saliva or urine of the patient. Melatonin is a hormone secreted by the pineal gland into the bloodstream and the CSF as a function of exposure of the optic nerve to light, which synchronizes the patient's circadian rhythm. In particular, increased levels of melatonin during evening hours may cause physiological changes in patient 12, which, in turn, may cause patient 12 to attempt to fall asleep.

IMD 18 may, for example, detect an increase in the level of melatonin in a bodily fluid, and estimate the time that patient 12 will attempt to fall asleep based on the detection.

For example, IMD 18 may compare the melatonin level or rate of change in the melatonin level to a threshold level, and identify the time that threshold value is exceeded. IMD 18 may identify the time that patient 12 is attempting to fall asleep as the time that the threshold is exceeded, or some amount of time after the threshold is exceeded.

IMD 18 may identify the time at which patient 12 has fallen asleep based on the activity level of the patient and/or one or more of the other physiological parameters that may be monitored by IMD 18 as indicated above. For example, IMD 18 may identify a discernable change, e.g., a decrease, in one or more physiological parameters, or the variability of one or more physiological parameters, which may indicate that patient 12 has fallen asleep. In some embodiments, IMD 18 determines a sleep probability metric value based on a value of a physiological parameter monitored by the medical device. In such embodiments, the sleep probability metric value may be compared to a threshold to identify when the patient has fallen asleep. In some embodiments, a sleep probability metric value is determined based on a value of each of a plurality of physiological parameters, the sleep probability values are averaged or otherwise combined to provide an overall sleep probability metric value, and the overall sleep probability metric value is compared to a threshold to identify the time that the patient falls asleep.

Other sleep quality metrics include total time sleeping per day, and the amount or percentage of time sleeping during nighttime or daytime hours per day. In some embodiments, IMD 18 may be able to detect arousal events during sleep based on one or more monitored physiological parameters, and the number of arousal events per night may be determined as a sleep quality metric. Further, in some embodiments IMD 18 may be able to determine in which sleep state patient 12 is, e.g., rapid eye movement (REM), S1, S2, S3, or S4, based on the EEG and/or one or more other monitored physiological parameters. The amount of time per day spent in these various sleep states may be a sleep quality metric. Detecting certain sleep states may be useful for evaluation of the quality of sleep of patient 12.

For example, the S3 and S4 sleep states may be of particular importance to the quality of sleep experienced by patient 12. Interruption from reaching these states, or inadequate time per night spent in these states, may cause patient 12 to not feel rested. For this reason, the S3 and S4 sleep states are believed to provide the "refreshing" part of sleep.

In some cases, interruption from reaching the S3 and S4 sleep states, or inadequate time per night spent in these states may increase the number or severity of epileptic seizures, movement or psychological disorder symptoms, or chronic pain. For this reason, in some embodiments, IMD 18 may determine an amount or percentage of time spent in one or both of the S3 and S4 sleep states as a sleep quality metric.

In embodiments in which IMD 18 is used to detect and treat epileptic events, detecting sleep states based on the EEG may be difficult. This is because epileptic events may be incorrectly classified as "sleep spindles," which are present in the EEG during sleep and may be used to detect sleep states. In some embodiments, as will be described below, an EEG signal may be filtered and analyzed, as well as statistically combined with other physiological parameters, to minimize the possibility of falsely detecting sleep or a sleep state.

In some embodiments, IMD 18 may determine average or median values of one or more sleep quality metrics over greater periods of time, e.g., a week or a month, as the value of the sleep quality metric. Further, in embodiments in which IMD 18 collects values for a plurality of the sleep quality metrics identified above, IMD 18 may determine a value for an overall sleep quality metric based on the collected values for the plurality of sleep quality metrics. IMD 18 may determine the value of an overall sleep quality metric by applying a function or look-up table to a plurality of sleep quality metric values, which may also include the application of weighting factors to one or more of the individual sleep quality metric values.

In some embodiments, IMD 18 may identify the current set of therapy parameters when a value of one or more sleep quality metrics is collected, and may associate that value with the current therapy parameter sets. For example, for each of a plurality therapy parameter sets used over time by IMD 18 to deliver therapy to patient 12, IMD 18 may store a representative value of each of one or more sleep quality metrics in a memory with an indication of the therapy parameter set with which that representative value is associated. A representative value of sleep quality metric for a therapy parameter set may be the mean or median of collected sleep quality metric values that have been associated with that therapy parameter set.

Programmer 28 may receive sleep quality metric values from IMD 18, and may provide sleep quality information to a user based on the sleep quality metric values. For example, programmer 28 may provide a message to patient 12, e.g., via a display, related to sleep quality based on received sleep quality metric values. Programmer 28 may, for example, suggest that patient 12 visit a clinician for prescription of sleep medication or for an adjustment to the therapy delivered by IMD 18. As other examples, programmer 28 may suggest that patient 12 increase the intensity of therapy delivered by IMD 18 during nighttime hours relative to previous nights, or select a different therapy parameter set for use by IMD 18 than the patient had selected during previous nights. Further, programmer 28 may report the quality of the patient's sleep to patient 12 to provide patient 12 with an objective indication of whether his or her sleep quality is good, adequate, or poor. Programmer 28 may also present a graphical representation of the sleep quality metric values, such as a trend diagram of values of one or more sleep quality metrics over time, or a histogram or pie chart illustrating percentages of time that a sleep quality metric was within various value ranges.

In embodiments in which IMD 18 associates sleep quality metric values with therapy parameter sets, programmer 28 may receive representative values for one or more sleep quality metrics from IMD 18 and information identifying the therapy parameter sets with which the representative values are associated. Using this information, programmer 28 may display a list of the therapy parameter sets to the clinician ordered according to their associated representative sleep quality metric values. The clinician may use such a list to identify effective or ineffective therapy parameter sets. Where a plurality of sleep quality metric values are collected, clinician programmer 28 may order the list according to values of a user-selected one of the sleep quality metrics. In this manner, the clinician may quickly identify the therapy parameter sets producing the best results in terms of sleep quality.

Alternatively, IMD 18 or programmer 28 may present this information to patient 12 or otherwise suggest to the patient whether the therapy parameter set should be changed to improve sleep quality. In other embodiments, IMD 18 or programmer 28 may autonomously make changes to the therapy parameter set based on the sleep quality metric values. For example, one of a plurality of therapy parameter sets may automatically be selected to control delivery of therapy based on the sleep quality metric values associated with the therapy parameter sets.

Figure 2:
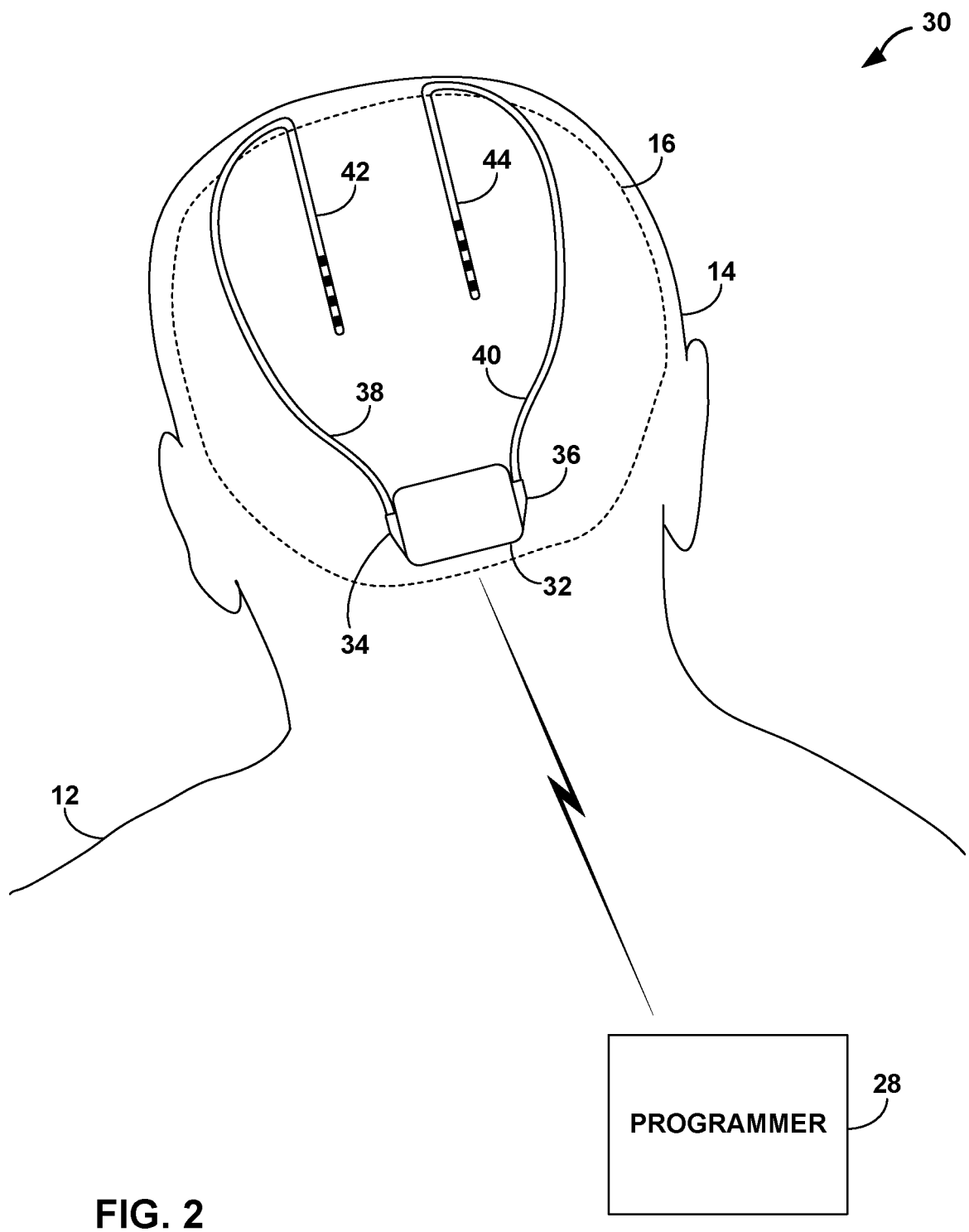
FIG. 2 is a conceptual diagram illustrating another example system that includes an implantable medical device implanted under the scalp that collects sleep quality information.

FIG. 2 is a conceptual diagram illustrating another example system 30 that includes an IMD 32 that collects sleep quality information. System 30 includes IMD 32, connection ports 34 and 36, leads 42 and 44 implanted within brain 16, and programmer 28. IMD 32 is substantially similar to IMD 18 of FIG. 1. However, IMD 32 is configured to be implanted beneath the scalp of head 14. In some embodiments, IMD 32 may be implanted at least partially within the skull of patient 12, e.g., within a recess or hole formed in or through the skull. Implanting IMD 32 in head 14 of patient 12 may reduce the length of leads 42 and 44 and reduce number of areas that must be surgically altered in the patient for implantation of the IMD.

Implantation of an IMD in head 14, as illustrated in FIG. 2, is an alternative to implantation of an IMD within the chest of the patient, as illustrated in FIG. 1. However, the invention is not limited to the implantation locations illustrated in FIGS. 1 and 2. An IMD that collects sleep quality information according to the invention may be implanted anywhere within a patient.

Leads 42 and 44 are tunneled from IMD 32 under the scalp of patient 12 to the location where each lead enters the skull of patient 12. Similar to leads 24 and 26 of FIG. 1, leads 42 and 44 are symmetrical or stereotactic leads, i.e., both leads are implanted at similar locations in each the right and left hemisphere of brain 16. In this manner, IMD 32 may deliver stimulation to bilateral locations within brain 16. Other therapies may also be provided via leads 42 and 44 or other leads coupled to IMD 32. In some embodiments, connection ports 34 and 36 may be located at a different location on IMD 32 to provide alternative positions of leads 42 and 44.

IMD 32 may be specifically designed to be implanted in head 14 of patient 12. IMD 32 may have a thin profile to minimize the protrusion of the IMD away from the skull. IMD 32 may be approximately rectangular in shape; however, the IMD may be closer in shape to a circle, square, oval, trapezoid, or other shape that best fits into the implantation site. In some embodiments, IMD 32 may include a compliant outer covering, which may at least partially cover or encapsulate a more rigid housing. IMD 32 may include separated components or multiple smaller modules within such a covering, which may enable IMD 32 to have a thinner profile.

As mentioned above with respect to system 10, system 30 may be capable of delivering electrical stimulation therapy and collecting sleep information. The sleep information may be collected by monitoring at least one physiological parameter that may be indicative of the sleep state of patient 12. IMD 32, similar to IMD 18 of FIG. 1, may determine sleep quality metric values based upon the monitored physiological parameters. IMD 32 may internally assign the sleep quality metric values to the current therapy parameter set. In alternative embodiments, IMD 32 may transmit the sleep quality metric values to programmer 28. Programmer 28 may then assign the sleep quality metric values to the current therapy parameter set. As described in FIG. 1, programmer 28 may be a clinician or patient programmer.

Figure 3:
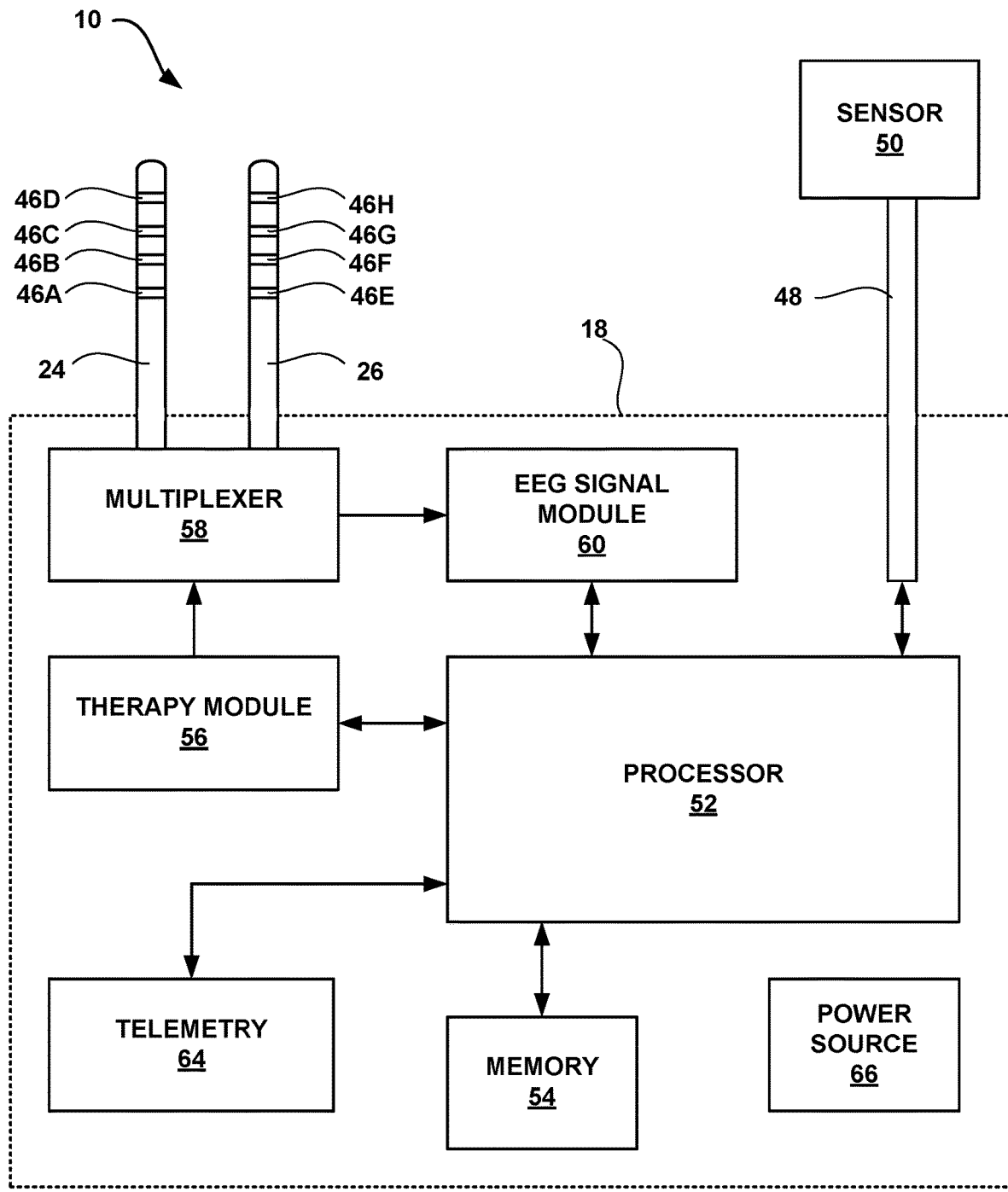
FIG. 3 is a block diagram illustrating the example system and implantable medical device of FIGS. 1 and 2.

FIG. 3 is a block diagram illustrating the example system and implantable medical device of FIGS. 1 and 2. IMD 18 of system 10 is shown as an example in FIG. 3; however, the block diagram may also be applicable to similar IMD 32 of system 30. FIG. 3 illustrates an example configuration of IMD 18 and leads 24 and 26. FIG. 3 also illustrates sensors 50A and 50B (collectively "sensors 50") that generate signals as a function of one or more physiological parameters of patient 12. As will be described in greater detail below, IMD 18 monitors physiological parameter signals received via leads 24, 26 and/or from one or more sensors 50 to determine values for one or more metrics that are indicative of sleep quality.

Some techniques for determining sleep quality metrics include monitoring an EEG signal of patient 12 received via leads 24, 26. For example, in some embodiments, IMD 18 may analyze the EEG signal to identify when the patient is asleep, or within which sleep state, i.e., S1, S2, S3, S4, or REM sleep state, patient 12 is. As will be described herein, IMD 18 may filter the EEG to analyze certain frequencies associated with certain sleep states.

IMD 18 may deliver neurostimulation therapy via electrodes 46A-D of lead 24 and electrodes 46E-46H of lead 26 (collectively "electrodes 46"). Electrodes 46 may be ring electrodes. The configuration, type and number of electrodes 46 illustrated in FIG. 3 are merely exemplary. For example, leads 24 and 26 may each include eight or any other number of electrodes 46, and the electrodes 46 need not be arranged linearly on each of leads 24 and 26 or be ring electrodes.

Electrodes 46 are electrically coupled to a multiplexer 58. Multiplexer 58 is able to selectively couple each of the electrodes to circuits within IMD 18 under the control of a processor 52. For example, through multiplexer 58, processor 52 may selectively couple electrodes 46 to a therapy module 56 or EEG signal module 60.

Therapy module 56 may, for example, include an output pulse generator coupled to a power source 66, which may include a primary or rechargeable battery. Therapy module 56 may deliver electrical pulses to patient 12 via at least some of electrodes 46 under the control of a processor 52, which controls therapy delivery module 56 to deliver neurostimulation therapy according to a current therapy parameter set. However, the invention is not limited to implantable neurostimulator embodiments or even to IMDs that deliver electrical stimulation. For example, in some embodiments a therapy delivery module 56 of an IMD may include a pump, circuitry to control the pump, and a reservoir to store a therapeutic agent for delivery via the pump. Further, in some embodiments, therapy delivery module 56 may deliver a thermal therapy, e.g., may include or be coupled to thermal transducer, such as Peltier effect device. The therapy parameter sets used by processor 52 to control delivery therapy by therapy module 56 may be received via a telemetry module 64 and/or stored in memory 54.

Processor 52 may include a microprocessor, a controller, a digital signal processor (DSP), an application specific integrated circuit (ASIC), a field-programmable gate array (FPGA), discrete logic circuitry, or the like. Memory 54 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 54 stores program instructions that, when executed by processor 52, cause IMD 18 and processor 52 to perform the functions attributed to them herein.

EEG signal module 60 receives signals from a selected set of the electrodes 46 via multiplexer 58 as controlled by processor 52. EEG signal module 60 may analyze the EEG signal for certain features indicative of sleep or different sleep states, and provide indications of relating to sleep or sleep states to processor 52. IMD 18 may include circuitry (not shown) that conditions the EEG signal such that it may be analyzed by processor 52. For example, IMD 18 may include one or more analog to digital converters to convert analog signals generated by sensor 50 into digital signals usable processor 52, as well as suitable filter and amplifier circuitry.

In some embodiments, processor 52 will only request EEG signal module 60 to operate when one or more other physiological parameters indicate that patient 12 is already asleep. However, processor 52 may also direct EEG signal module to analyze the EEG signal to determine whether patient 12 is sleeping, and such analysis may be considered alone or in combination with other physiological parameters to determine whether patient 12 is asleep. In some embodiments, the functionality of EEG signal module 60 may be provided by processor 52, which, as described above, may include one or more microprocessors, ASICs, or the like.

Sensors 50 generate a signal as a function of one or more physiological parameters of patient 12. IMD 18 may include circuitry (not shown) that conditions the signals generated by sensors 50 such that they may be analyzed by processor 52, e.g., analog-to-digital converters, amplifiers, and/or filters. Although shown as including two sensors 50, system 10 may include any number of sensors.

Further, as illustrated by FIG. 3, sensors 50 may be included as part of IMD 18, or coupled to IMD 18 via lead 48, as illustrated in FIG. 3. Lead 48 may be bundled with leads 24 and 26 in some embodiments. Further, is some embodiments, a sensor 50 may be coupled to IMD 18 via therapy leads 24 and 26. In some embodiments, a sensor 50 located outside of IMD 18 may be in wireless communication with IMD 18. Wireless communication between sensor 50 and IMD 18 may, as examples, include RF communication or communication via electrical signals conducted through the tissue and/or fluid of patient 12.

As discussed above, exemplary physiological parameters of patient 12 that may be monitored by IMD 18 to determine values of one or more sleep quality metrics include activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, the level of melatonin within a bodily fluid of patient 12, electrical activity of the brain of the patient, e.g., EEG or EEG morphology, and eye motion. Further, as discussed above, in some external medical device embodiments of the invention, galvanic skin response may additionally or alternatively be monitored. Sensors 50 may include any type of sensor known in the art capable of generating a signal as a function of one or more of these parameters. In some embodiments, processor 52 may receive an EEG signal from sensors 50 instead of electrodes 46.

In some embodiments, in order to determine one or more sleep quality metric values, processor 52 determines when patient 12 is attempting to fall asleep. For example, processor 52 may identify the time that patient begins attempting to fall asleep based on an indication received from patient 12, e.g., via programmer 28 and a telemetry circuit 64. In other embodiments, processor 52 identifies the time that patient 12 begins attempting to fall asleep based on the activity level of patient 12.

In such embodiments, IMD 18 may include one or more sensors 50 that generate a signal as a function of patient activity. For example, sensors 50 may include one or more accelerometers, gyros, mercury switches, or bonded piezoelectric crystals that generates a signal as a function of patient activity, e.g., body motion, footfalls or other impact events, and the like. Additionally or alternatively, sensor 50 may include one or more electrodes that generate an electromyogram (EMG) signal as a function of muscle electrical activity, which may indicate the activity level of a patient. The electrodes may be, for example, located in the legs, abdomen, chest, back or buttocks of patient 12 to detect muscle activity associated with walking, running, or the like. The electrodes may be coupled to IMD 18 wirelessly or by lead 48 or, if IMD 18 is implanted in these locations, integrated with a housing of IMD 18.

However, bonded piezoelectric crystals located in these areas generate signals as a function of muscle contraction in addition to body motion, footfalls or other impact events. Consequently, use of bonded piezoelectric crystals to detect activity of patient 12 may be preferred in some embodiments in which it is desired to detect muscle activity in addition to body motion, footfalls, or other impact events. Bonded piezoelectric crystals may be coupled to IMD 18 wirelessly or via lead 48, or piezoelectric crystals may be bonded to the can of IMD 18 when the IMD is implanted in these areas, e.g., in the back, chest, buttocks or abdomen of patient 12.

Processor 52 may identify a time when the activity level of patient 12 falls below a threshold activity level value stored in memory 54, and may determine whether the activity level remains substantially below the threshold activity level value for a threshold amount of time stored in memory 54. In other words, patient 12 remaining inactive for a sufficient period of time may indicate that patient 12 is attempting to fall asleep. If processor 52 determines that the threshold amount of time is exceeded, processor 52 may identify the time at which the activity level fell below the threshold activity level value as the time that patient 12 began attempting to fall asleep.

In some embodiments, processor 52 determines whether patient 12 is attempting to fall asleep based on whether patient 12 is or is not recumbent, e.g., lying down. In such embodiments, sensors 50 may include a plurality of accelerometers, gyros, or magnetometers oriented orthogonally that generate signals which indicate the posture of patient 12. In addition to being oriented orthogonally with respect to each other, sensors 50 used to detect the posture of patient 12 may be generally aligned with an axis of the body of patient 12. In exemplary embodiments, IMD 18 includes three orthogonally oriented posture sensors 50.

When sensors 50 include accelerometers, for example, that are aligned in this manner, processor 52 may monitor the magnitude and polarity of DC components of the signals generated by the accelerometers to determine the orientation of patient 12 relative to the Earth's gravity, e.g., the posture of patient 12. In particular, the processor 52 may compare the DC components of the signals to respective threshold values stored in memory 54 to determine whether patient 12 is or is not recumbent. Further information regarding use of orthogonally aligned accelerometers to determine patient posture may be found in a commonly assigned U.S. Pat. No. 5,593,431, which issued to Todd J. Sheldon.

Sensors 50 that may generate a signal that indicates the posture of patient 12 may include electrodes that generate an electromyogram (EMG) signal, or bonded piezoelectric crystals that generate a signal as a function of contraction of muscles. This type of sensor 50 may be implanted in the legs, buttocks, chest, abdomen, or back of patient 12, as described herein. The signals generated by such sensors when implanted in these locations may vary based on the posture of patient 12, e.g., may vary based on whether the patient is standing, sitting, or lying down.

Further, changes of the posture of patient 12 may cause pressure changes within the cerebrospinal fluid (CSF) of the patient. Consequently, sensors 50 may include pressure sensors coupled to one or more intrathecal, intracerebroventricular, or subarachnoid catheters, or pressure sensors in such locations coupled to IMD 18 wirelessly or via lead 48. CSF pressure changes associated with posture changes may be particularly evident within the brain of the patient, e.g., may be particularly apparent in an intracranial pressure (ICP) waveform. While CSF pressure may be particularly practical as a means of detecting posture in cranially implanted IMD embodiments, or other embodiments with leads located in the brain, use of CSF pressure to detect posture is not limited to such embodiments.

In some embodiments, processor 52 considers both the posture and the activity level of patient 12 when determining whether patient 12 is attempting to fall asleep. For example, processor 52 may determine whether patient 12 is attempting to fall asleep based on a sufficiently long period of sub-threshold activity, as described above, and may identify the time that patient 12 began attempting to fall asleep as the time when patient 12 became recumbent.

In other embodiments, processor 52 determines when patient 12 is attempting to fall asleep based on the level of melatonin in a bodily fluid. In such embodiments, sensors 50 may include a chemical sensor that is sensitive to the level of melatonin or a metabolite of melatonin in the bodily fluid, and estimate the time that patient 12 will attempt to fall asleep based on the detection. For example, processor 52 may compare the melatonin level or rate of change in the melatonin level to a threshold level stored in memory 54, and identify the time that threshold value is exceeded. Processor 52 may identify the time that patient 12 is attempting to fall asleep as the time that the threshold is exceeded, or some amount of time after the threshold is exceeded. Any of a variety of combinations or variations of the above-described techniques may be used to determine when patient 12 is attempting to fall asleep, and a specific one or more techniques may be selected based on the sleeping and activity habits of a particular patient.

Processor 52 may also determine when patient 12 is asleep, e.g., identify the times that patient 12 falls asleep and wakes up, in order to determine one or more sleep quality metric values. The detected values of physiological parameters of patient 12, such as activity level, heart rate, ECG morphological features, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, EEG activity and/or morphology, eye motion and galvanic skin response may discernibly change when patient 12 falls asleep or wakes up. Some of these physiological parameters may be at low values when patient 12 is asleep. Further, the variability of at least some of these parameters, such as heart rate and respiration rate, may be at a low value when the patient is asleep.

Consequently, in order to detect when patient 12 falls asleep and wakes up, processor 52 may monitor one or more of these physiological parameters, or the variability of these physiological parameters, and detect the discernable changes in their values associated with a transition between a sleeping state and an awake a waking state. In some embodiments, processor 52 may determine a mean or median value for a parameter based on values of a signal over time, and determine whether patient 12 is asleep or awake based on the mean or median value. Processor 52 may compare one or more parameter or parameter variability values to thresholds stored in memory 54 to detect when patient 12 falls asleep or wakes. The thresholds may be absolute values of a physiological parameter, or time rate of change values for the physiological parameter, e.g., to detect sudden changes in the value of a parameter or parameter variability. In some embodiments, a threshold used by processor 52 to determine whether patient 12 is asleep may include a time component. For example, a threshold may require that a physiological parameter be above or below a threshold value for a period of time before processor 52 determines that patient 12 is awake or asleep.

In some embodiments, in order to determine whether patient 12 is asleep, processor 52 monitors a plurality of physiological parameters, and determines a value of a metric that indicates the probability that patient 12 is asleep for each of the parameters based on a value of the parameter. In particular, the processor 52 may apply a function or look-up table to the current, mean, or median value, and/or the variability of each of a plurality of physiological parameters to determine a sleep probability metric for each of the plurality of physiological parameters. A sleep probability metric value may be a numeric value, and in some embodiments may be a probability value, e.g., a number within the range from 0 to 1, or a percentage value.

Processor 52 may average or otherwise combine the plurality of sleep probability metric values to provide an overall sleep probability metric value. In some embodiments, processor 52 may apply a weighting factor to one or more of the sleep probability metric values prior to combination. Processor 52 may compare the overall sleep probability metric value to one or more threshold values stored in memory 54 to determine when patient 12 falls asleep or awakes. Use of sleep probability metric values to determine when a patient is asleep based on a plurality of monitored physiological parameters is described in greater detail in a commonly-assigned and copending U.S. patent application Ser. No. 11/081,786 by Ken Heruth and Keith Miesel, entitled "DETECTING SLEEP," which issued as U.S. Pat. No. 7,775,993, and is incorporated herein by reference in its entirety.

To enable processor 52 to determine when patient 12 is asleep or awake, sensors 50 may include, for example, activity sensors as described above. In some embodiments, the activity sensors may include electrodes or bonded piezoelectric crystals, which may be implanted in the back, chest, buttocks, or abdomen of patient 12 as described above. In such embodiments, processor 52 may detect the electrical activation and contractions of muscles associated with gross motor activity of the patient, e.g., walking, running or the like via the signals generated by such sensors. Processor 52 may also detect spasmodic, irregular, movement disorder or pain related muscle activation via the signals generated by such sensors. Such muscle activation may indicate that patient 12 is not sleeping, e.g., unable to sleep, or if patient 12 is sleeping, may indicate a lower level of sleep quality.

As another example, sensors 50 may include electrodes located on leads or integrated as part of the housing of IMD 18 that generate an electrogram signal as a function of electrical activity of the heart of patient 12, and processor 52 may monitor the heart rate of patient 12 based on the electrogram signal. In other embodiments, a sensor may include an acoustic sensor within IMD 18, a pressure or flow sensor within the bloodstream or cerebrospinal fluid of patient 12, or a temperature sensor located within the bloodstream of patient 12. The signals generated by such sensors may vary as a function of contraction of the heart of patient 12, and can be used by IMD 18 to monitor the heart rate of patient 12.

In some embodiments, processor 52 may detect, and measure values for one or more ECG morphological features within an electrogram generated by electrodes as described above. ECG morphological features may vary in a manner that indicates whether patient 12 is asleep or awake. For example, the amplitude of the ST segment of the ECG may decrease when patient 12 is asleep. Further, the amplitude of QRS complex or T-wave may decrease, and the widths of the QRS complex and T-wave may increase when patient 12 is asleep. The QT interval and the latency of an evoked response may increase when patient 12 is asleep, and the amplitude of the evoked response may decrease when patient 12 is asleep.

In some embodiments, sensor 50 may include an electrode pair including at least one electrode within or proximate to the thorax, e.g., an electrode integrated with the housing of IMD 18 or on a lead implanted at such a location, that generates a signal as a function of the thoracic impedance of patient 12, as described above. The thoracic impedance signal varies as a function of respiration by patient 12. In other embodiments, sensors 50 may include a strain gage, bonded piezoelectric element, or pressure sensor within the blood or cerebrospinal fluid that generates a signal that varies based on patient respiration. An electrogram generated by electrodes as discussed above may also be modulated by patient respiration, and may be used as an indirect representation of respiration rate.

Sensors 50 may include electrodes that generate an electromyogram (EMG) signal as a function of muscle electrical activity, as described above, or may include any of a variety of known temperature sensors to generate a signal as a function of a core or subcutaneous temperature of patient 12. Such electrodes and temperature sensors may be incorporated within the housing of IMD 18, or coupled to IMD 18 wirelessly via leads. Sensors 50 may also include a pressure sensor within, or in contact with, a blood vessel. The pressure sensor may generate a signal as a function of the a blood pressure of patient 12, and may, for example, comprise a Chronicle Hemodynamic Monitor™ commercially available from Medtronic, Inc. of Minneapolis, Minn. Further, certain muscles of patient 12, such as the muscles of the patient's neck, may discernibly relax when patient 12 is asleep or within certain sleep states. Consequently, sensors 50 may include strain gauges or EMG electrodes implanted in such locations that generate a signal as a function of muscle tone.

Sensors 50 may also include optical pulse oximetry sensors or Clark dissolved oxygen sensors located within, as part of a housing of, or outside of IMD 18, which generate signals as a function of blood oxygen saturation and blood oxygen partial pressure respectively. In some embodiments, system 10 may include a catheter with a distal portion located within the cerebrospinal fluid of patient 12, and the distal end may include a Clark dissolved oxygen sensor to generate a signal as a function of the partial pressure of oxygen within the cerebrospinal fluid. Embodiments in which an IMD comprises an implantable pump, for example, may include a catheter with a distal portion located in the cerebrospinal fluid.

In some embodiments, sensors 50 may include one or more intraluminal, extraluminal, or external flow sensors positioned to generate a signal as a function of arterial blood flow. A flow sensor may be, for example, an electromagnetic, thermal convection, ultrasonic-Doppler, or laser-Doppler flow sensor. Further, in some external medical device embodiments of the invention, sensors 50 may include one or more electrodes positioned on the skin of patient 12 to generate a signal as a function of galvanic skin response.

Also, the motion of the eyes of patient 12 may vary depending on whether the patient is sleeping and which sleep state the patient is in. Consequently, sensors 50 may include electrodes placed proximate to the eyes of patient 12 to detect electrical activity associated with motion of the eyes, e.g., to generate an electro-oculography (EOG) signal. Such electrodes may be coupled to IMD 18 via one or more lead 48, or may be included within modules that include circuitry to wirelessly transmit detected signals to IMD 18. Wirelessly coupled modules incorporating electrodes to detect eye motion may be worn externally by patient 12, e.g., attached to the skin of patient 12 proximate to the eyes by an adhesive when the patient is attempting to sleep.

Further, processor 52 may determine whether patient 12 is asleep based on indications received from EEG signal module 60 based on its analysis of the EEG received via electrodes 46. EEG signal module 60 may process the EEG signals to detect when patient 12 is asleep using any of a variety of techniques, such as techniques that identify whether a patient is asleep based on the amplitude and/or frequency of the EEG signals.

Processor 52 may also detect arousals and/or apneas that occur when patient 12 is asleep based on one or more of the above-identified physiological parameters. For example, processor 52 may detect an arousal based on an increase or sudden increase in one or more of heart rate, heart rate variability, respiration rate, respiration rate variability, blood pressure, or muscular activity as the occurrence of an arousal. Processor 52 may detect an apnea based on a disturbance in the respiration rate of patient 12, e.g., a period with no respiration.

Processor 52 may also detect arousals or apneas based on sudden changes in one or more of the ECG morphological features identified above. For example, a sudden elevation of the ST segment within the ECG may indicate an arousal or an apnea. Further, sudden changes in the amplitude or frequency of an EEG signal, EOG signal, or muscle tone signal may indicate an apnea or arousal. Memory 54 may store thresholds used by processor 52 to detect arousals and apneas. Processor 52 may determine, as a sleep quality metric value, the number of apnea events and/or arousals during a night.

Further, in some embodiments, processor 52 may determine which sleep state patient 12 is in during sleep, e.g., REM, S1, S2, S3, or S4, based on one or more of the monitored physiological parameters, and/or indications received from EEG signal module 60. In some embodiments, memory 54 may store one or more thresholds for each of sleep states, and processor 52 may compare physiological parameter or sleep probability metric values to the thresholds to determine which sleep state patient 12 is currently in.

Further, in some embodiments, EEG signal module 60 may use any of a variety of techniques for determining which sleep state patient is in based on an EEG signal, which processor 52 may receive via electrodes 46 as described above, such as techniques that identify sleep state based on the amplitude and/or frequency of the EEG signals. In some embodiments, processor 52 may also determine which sleep state patient is in based on an EOG signal, which processor 52 may receive via electrodes as described above, either alone or in combination with indications received from EEG signal module 60.

Figure 4:
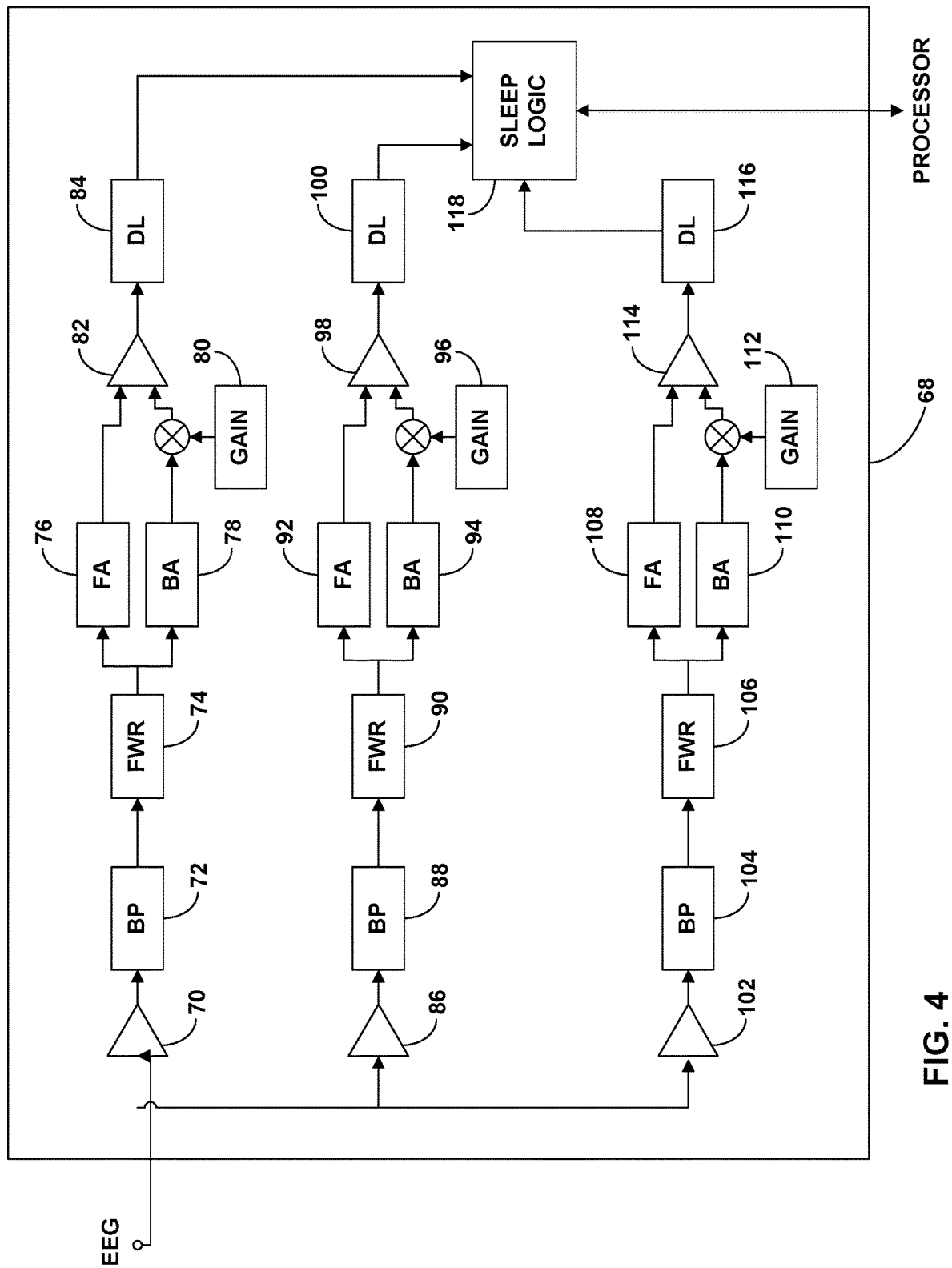
FIG. 4 is a logic diagram illustrating an example circuit that detects the sleep state of a patient from the electroencephalogram (EEG) signal.

FIG. 4 is a logical diagram of an example circuit that detects the sleep type of a patient based on the electroencephalogram (EEG) signal. As shown in FIG. 4, module 68 may be integrated into EEG signal module 60 of FIG. 3. An EEG signal detected by electrodes 46 is transmitted into module 68 and provided to three channels, each of which includes a respective one of amplifiers 70, 86, and 102, and bandpass filters 72, 88 and 104. In other embodiments, a common amplifier amplifies the EEG signal prior to filters 72, 88, and 104.

Bandpass filter 72 allows frequencies between approximately 4 Hz and approximately 8 Hz, and signals within the frequency range may be prevalent in the EEG during S1 and S2 sleep states. Bandpass filter 88 allows frequencies between approximately 1 Hz and approximately 3 Hz, which may be prevalent in the EEG during the S3 and S4 sleep states. Bandpass filter 104 allows frequencies between approximately 10 Hz and approximately 50 Hz, which may be prevalent in the EEG during REM sleep. Each resulting signal may then be processed to identify in which sleep state patient 12 is.

After bandpass filtering of the original EEG signal, the filtered signals are similarly processed in parallel before being delivered to sleep logic module 118. For ease of discussion, only one of the three channels will be discussed herein, but each of the filtered signals would be processed similarly.

Once the EEG signal is filtered by bandpass filter 72, the signal is rectified by full-wave rectifier 74. Modules 76 and 78 respectively determine the foreground average and background average so that the current energy level can be compared to a background level at comparator 82. The signal from background average is increased by gain 80 before sent to comparator 82, because comparator 82 operates in the range of millivolts or volts while the EEG signal amplitude is originally on the order of microvolts. The signal from comparator 82 is indicative of sleep stages S1 and S2. If duration logic 84 determines that the signal is greater than a predetermined level for a predetermined amount of time, the signal is sent to sleep logic module 118 indicating that patient 12 may be within the S1 or S2 sleep states. In some embodiments, as least duration logic 84, 100, 116 and sleep logic 118 may be embodied in processor 52 (FIG. 3).

Module 68 may detect all sleep types for patient 12. Further, the beginning of sleep may be detected by module 68 based on the sleep state of patient 12. Some of the components of module 68 may vary from the example of FIG. 4. For example, gains 80, 96 and 112 may be provided from the same power source. Module 68 may be embodied as analog circuitry, digital circuitry, or a combination thereof.

In other embodiments, FIG. 4 may not need to reference the background average to determine the current state of sleep of patient 12. Instead, the power of the signals from bandpass filters 72, 88, and 104 are compared to each other, and sleep logic module 118 determines which the sleep state of patient 12 based upon the frequency band that has the highest power. In this case, the signals from full-wave rectifiers 74, 90, and 106 are sent directly to a device that calculates the signal power, such as a spectral power distribution module (PSD), and then to sleep logic module 118 which determines the frequency band of the greatest power, e.g., the sleep state of patient 12. In some cases, the signal from full-wave rectifiers 74, 90, and 106 may be normalized by a gain component to correctly weight each frequency band.

Figure 5:
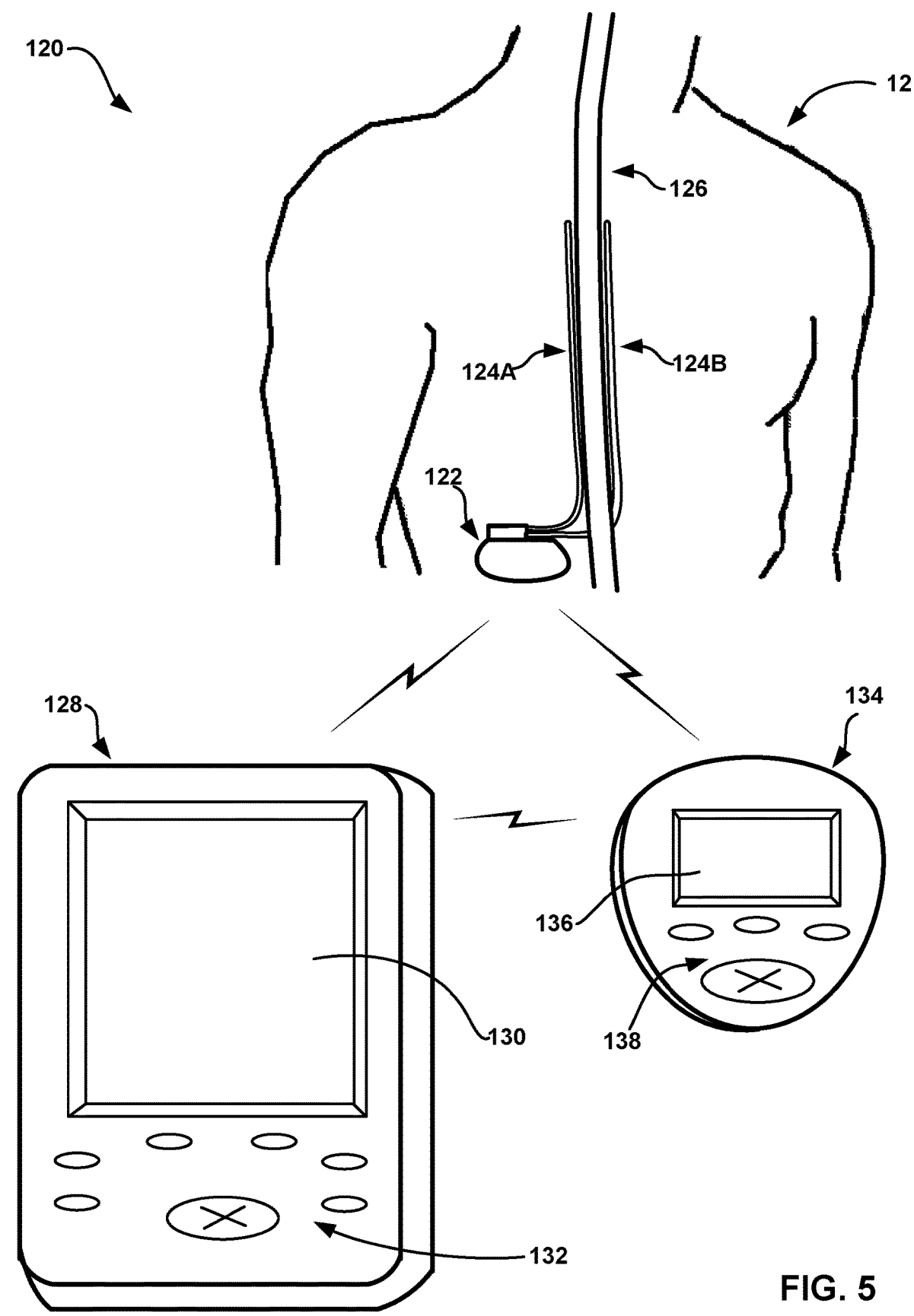
FIG. 5 is a conceptual diagram illustrating another example system that includes an implantable medical device that collects sleep quality information according to the invention.

FIG. 5 is a conceptual diagram illustrating another example system 120 that includes an implantable medical device (IMD) 122 that collects information relating to the quality of sleep experienced by a patient 12 according to the invention. System 120 may be substantially similar in function to systems 10 and 30 of FIGS. 1 and 3, respectively. IMD 122 may be similar to IMDs 18 and 32, and may determine sleep quality metric values based on physiological parameter signals generated by sensors as discussed above with respect to IMD 18. However, unlike IMDs 18 and 32, IMD 122 delivers spinal cord stimulation (SCS) via leads 124A and 124B (collectively "leads 124") implanted proximate to the spinal cord 126 of patient 12 in order to, for example, reduce pain experienced by patient 12.

Like the IMDs discussed above, IMD 122 delivers therapy according to a set of therapy parameters, i.e., a set of values for a number of parameters that define the therapy delivered according to that therapy parameter set, which may include voltage or current pulse amplitudes, pulse widths, pulse rates, and information identifying which electrodes (not shown) on leads 124 have been selected for delivery of pulses, and the polarities of the selected electrodes.

FIG. 5 also illustrates system 120 as including a clinician programmer 128 and a patient programmer 134. Clinician programmer 128 and patient programmer 134 may be similar to programmer 28 of FIGS. 1 and 2. A clinician (not shown) may use clinician programmer 128 to program therapy for patient 12, e.g., specify a number of therapy parameter sets and provide the parameter sets to IMD 122. The clinician may also use clinician programmer 128 to retrieve information collected by IMD 122. The clinician may use clinician programmer 128 to communicate with IMD 122 both during initial programming of IMD 122, and for collection of information and further programming during follow-up visits.

Clinician programmer 128 may, as shown in FIG. 5, be a handheld computing device. Clinician programmer 128 includes a display 130, such as a LCD or LED display, to display information to a user. Clinician programmer 128 may also include a keypad 132, which may be used by a user to interact with clinician programmer 128. In some embodiments, display 130 may be a touch screen display, and a user may interact with clinician programmer 128 via display 130. A user may also interact with clinician programmer 128 using peripheral pointing devices, such as a stylus or mouse. Keypad 132 may take the form of an alphanumeric keypad or a reduced set of keys associated with particular functions.

Patient programmer 134 also may, as shown in FIG. 5, be a handheld computing device. Patient 12 may use patient programmer 134 to control the delivery of therapy by IMD 122. For example, using patient programmer 134, patient 12 may select a current therapy parameter set from among the therapy parameter sets preprogrammed by the clinician, or may adjust one or more parameters of a preprogrammed therapy parameter set to arrive at the current therapy parameter set.

Patient programmer 134 may include a display 136 and a keypad 138, to allow patient 12 to interact with patient programmer 134. In some embodiments, display 136 may be a touch screen display, and patient 12 may interact with patient programmer 134 via display 136. Patient 12 may also interact with patient programmer 134 using peripheral pointing devices, such as a stylus, mouse, or the like.

However, clinician and patient programmers 128, 134 are not limited to the hand-held computer embodiments illustrated in FIG. 5. Programmers 128, 134 according to the invention may be any sort of computing device. For example, a programmer 128, 134 according to the invention may be a tablet-based computing device, a desktop computing device, or a workstation.

IMD 122, clinician programmer 128 and patient programmer 134 may, as shown in FIG. 5, communicate via wireless communication. Clinician programmer 128 and patient programmer 134 may, for example, communicate via wireless communication with IMD 122 using radio frequency (RF) telemetry techniques known in the art. Clinician programmer 128 and patient programmer 134 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 128 and patient programmer 134 need not communicate wirelessly, however. For example, programmers 128 and 134 may communicate via a wired connection, such as via a serial communication cable, or via exchange of removable media, such as magnetic or optical disks, or memory cards or sticks. Further, clinician programmer 128 may communicate with one or both of IMD 122 and patient programmer 134 via remote telemetry techniques known in the art, communicating via a local area network (LAN), wide area network (WAN), public switched telephone network (PSTN), or cellular telephone network, for example.

One or both of programmers 128, 134 may receive sleep quality metric values from IMD 122, and may provide sleep quality information to a user based on the sleep quality metric values. For example, patient programmer 134 may provide a message to patient 12, e.g., via display 136, related to sleep quality based on received sleep quality metric values. Patient programmer 134 may, for example, suggest that patient 12 visit a clinician for prescription of sleep medication or for an adjustment to the therapy delivered by IMD 122. As other examples, patient programmer 134 may suggest that patient 12 increase the intensity of therapy delivered by IMD 122 during nighttime hours relative to previous nights, or select a different therapy parameter set for use by IMD 122 than the patient had selected during previous nights. Further, patient programmer 134 may report the quality of the patient's sleep to patient 12 to, for example, provide patient 12 with an objective indication of whether his or her sleep quality is good, adequate, or poor.

Figure 6:
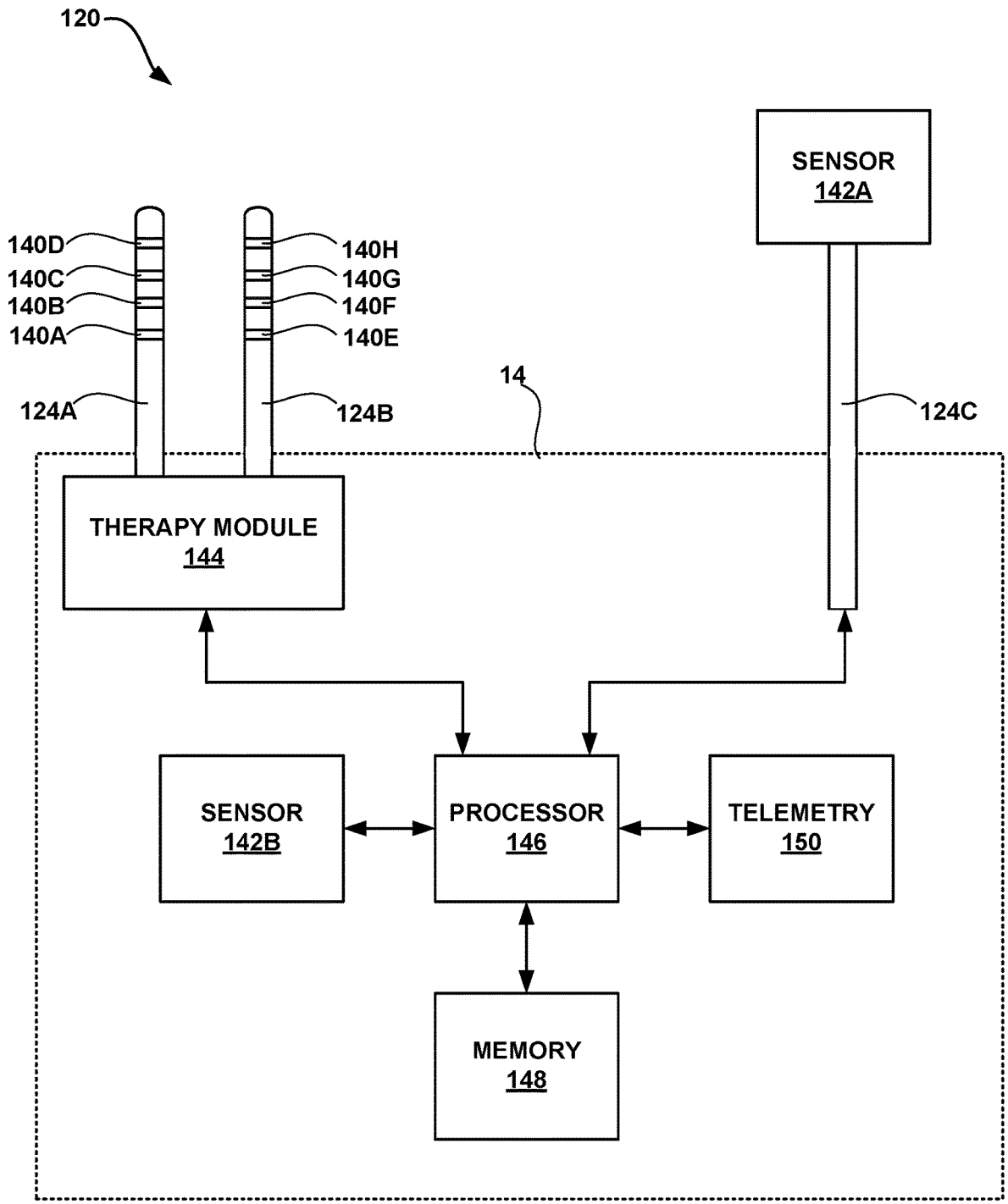
FIG. 6 is a block diagram further illustrating the example system and implantable medical device of FIG. 5.

FIG. 6 is a block diagram further illustrating system 120. System 120 may function similar to systems 10 and 30 as described in FIG. 3. In particular, FIG. 6 illustrates an example configuration of IMD 122 and leads 124A and 124B. FIG. 6 also illustrates sensors 142A and 142B (collectively "sensors 142") that generate signals as a function of one or more physiological parameters of patient 12, which may be substantially similar to sensors 50 discussed above with respect to FIG. 3.

In the illustrated example, IMD 122 is coupled to leads 124A and 124B, which respectively include electrodes 140A-140D and electrodes 140E-140H (collectively "electrodes 140"). Electrodes 140 may be ring electrodes. The configuration, type and number of electrodes 140 illustrated in FIG. 6 are merely exemplary.

Electrodes 140 are electrically coupled to a therapy delivery module 144 via leads 124, which may be substantially similar to therapy module 56 discussed above with respect to FIG. 3. Further, IMD 122 includes a processor 146, memory 148 and telemetry module 150 substantially similar to and providing substantially the same functionality as the processor 52, memory 54 and telemetry module 64 of FIG. 3.

Because leads 124 are not implanted within or proximate to brain, IMD 122 does not include an EEG signal module 60 in the illustrated embodiment. In other embodiments, IMD 122 may nonetheless monitor the EEG as described above. In such embodiments, IMD 122 may include an EEG signal module 60, or processor 146 may provide similar functionality. In such embodiments, sensors 142 may include one or more electrodes positioned within or proximate to the brain of patient 12, which detect electrical activity of the brain. Processor 146 may be wirelessly coupled to electrodes that detect brain electrical activity.

For example, one or more modules may be implanted beneath the scalp of the patient, each module including a housing, one or more electrodes, and circuitry to wirelessly transmit the signals detected by the one or more electrodes to IMD 122. In other embodiments, the electrodes may be applied to the patient's scalp, and electrically coupled to a module that includes circuitry for wirelessly transmitting the signals detected by the electrodes to IMD 122. The electrodes may be glued to the patient's scalp, or a head band, hair net, cap, or the like may incorporate the electrodes and the module, and may be worn by patient 12 to apply the electrodes to the patient's scalp when, for example, the patient is attempting to sleep. The signals detected by the electrodes and transmitted to IMD 122 may be electroencephalogram (EEG) signals, and processor 146 may process the EEG signals to detect when patient 12 is asleep using any of a variety of known techniques, such as techniques that identify whether a patient is asleep based on the amplitude and/or frequency of the EEG signals. FIGS. 3 and 4 describe methods for analyzing and processing the EEG signal.

Figure 7:
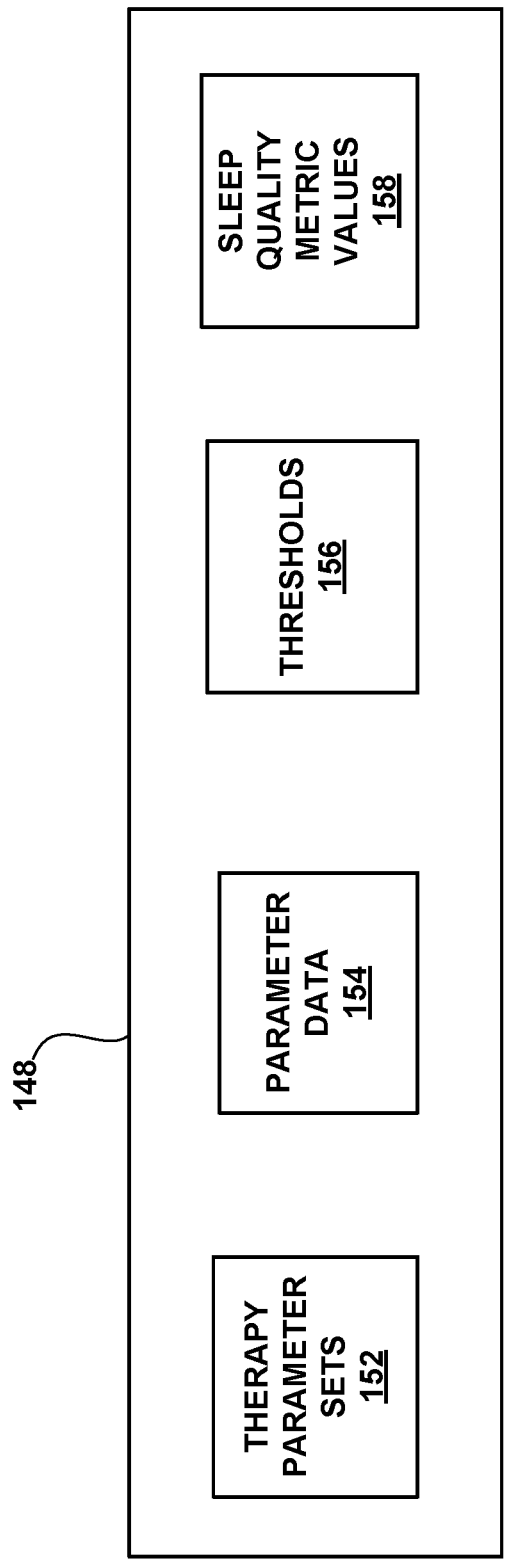
FIG. 7 is a block diagram illustrating an example memory of an implantable medical device that collects sleep quality information.

FIG. 7 further illustrates memory 148 of IMD 122, to which memories 54 of IMDs 18 and 32 may be substantially similar. As illustrated in FIG. 7, memory 148 stores information describing a plurality of therapy parameter sets 152. Therapy parameter sets 152 may include parameter sets specified by a clinician using clinician programmer 128. Therapy parameter sets 152 may also include parameter sets that are the result of patient 12 changing one or more parameters of one of the preprogrammed therapy parameter sets via patient programmer 134.

Memory 148 may also include parameter information 154 recorded by processor 146, e.g., physiological parameter values, or mean or median physiological parameter values. Memory 148 stores threshold values 156 used by processor 146 in the collection of sleep quality metric values, as discussed above. In some embodiments, memory 148 also stores one or more functions or look-up tables (not shown) used by processor 146 to determine sleep probability metric values, or to determine an overall sleep quality metric value.

Further, processor 146 stores determined values 158 for one or more sleep quality metrics within memory 148. Processor 146 may collect sleep quality metric values 158 each time patient 12 sleeps, or only during selected times that patient 12 is asleep. Processor 146 may store each sleep quality metric value determined within memory 148 as a sleep quality metric value 158, or may store mean or median sleep quality metric values over periods of time such as weeks or months as sleep quality metric values 158. Further, processor 146 may apply a function or look-up table to a plurality of sleep quality metric values to determine overall sleep quality metric value, and may store the overall sleep quality metric values within memory 148. The application of a function or look-up table by processor 146 for this purpose may involve the use or weighting factors for one or more of the individual sleep quality metric values.

In some embodiments, processor 146 identifies which of therapy parameter sets 152 is currently selected for use in delivering therapy to patient 12 when a value of one or more sleep quality metrics is collected, and may associate that value with the current therapy parameter set. For example, for each of the plurality of therapy parameter sets 152, processor 146 may store a representative value of each of one or more sleep quality metrics within memory 148 as a sleep quality metric value 158 with an indication of which of the therapy parameter sets that representative value is associated with. A representative value of sleep quality metric for a therapy parameter set may be the mean or median of collected sleep quality metric values that have been associated with that therapy parameter set.

As shown in FIG. 6, IMD 122 also includes a telemetry circuit 150 that allows processor 146 to communicate with clinician programmer 128 and patient programmer 134. Processor 146 may receive information identifying therapy parameter sets 152 preprogrammed by the clinician and threshold values 156 from clinician programmer 128 via telemetry circuit 150 for storage in memory 148. Processor 146 may receive an indication of the therapy parameter set 152 selected by patient 12 for delivery of therapy, or adjustments to one or more of therapy parameter sets 152 made by patient 12, from patient programmer 134 via telemetry circuit 150. Programmers 128, 134 may receive sleep quality metric values 158 from processor 146 via telemetry circuit 150.

Figure 8:
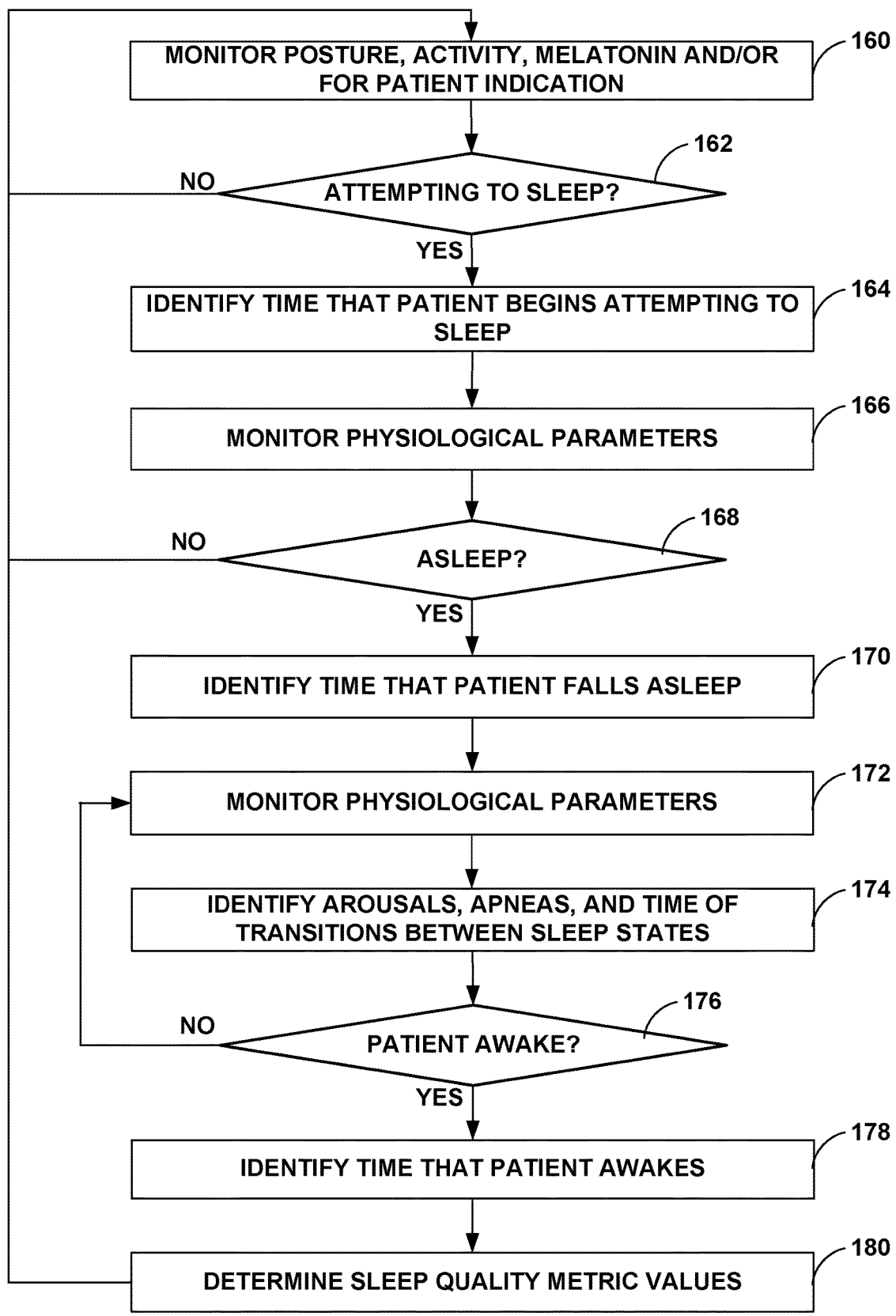
FIG. 8 is a flow diagram illustrating an example method for collecting sleep quality information that may be employed by an implantable medical device.

FIG. 8 is a flow diagram illustrating an example method for collecting sleep quality information that may be employed by any of IMDs 18, 32 and 122, but IMD 18 will be used herein as an example. IMD 18 monitors the posture, activity level, and/or melatonin level of patient 12, or monitors for an indication from patient 12, e.g., via patient programmer 28 (160), and determines whether patient 12 is attempting to fall asleep based on the posture, activity level, melatonin level, and/or a patient indication, as described above (162). If IMD 18 determines that patient 12 is attempting to fall asleep, IMD 18 identifies the time that patient 12 began attempting to fall asleep using any of the techniques described above (164), and monitors one or more of the various physiological parameters of patient 12 discussed above to determine whether patient 12 is asleep (166, 168).

In some embodiments, IMD 18 compares parameter values or parameter variability values to one or more threshold values 156 to determine whether patient 12 is asleep. In other embodiments, IMD 18 applies one or more functions or look-up tables to determine one or more sleep probability metric values based on the physiological parameter values, and compares the sleep probability metric values to one or more threshold values 156 to determine whether patient 12 is asleep. While monitoring physiological parameters (166) to determine whether patient 12 is asleep (168), IMD 18 may continue to monitor the posture and/or activity level of patient 12 (160) to confirm that patient 12 is still attempting to fall asleep (162).

When IMD 18 determines that patient 12 is asleep, e.g., by analysis of the various parameters contemplated herein, IMD 18 will identify the time that patient 12 fell asleep (170). While patient 12 is sleeping, IMD 18 will continue to monitor physiological parameters of patient 12 (172). As discussed above, IMD 18 may identify the occurrence of arousals and/or apneas based on the monitored physiological parameters (174). Further, IMD 18 may identify the time that transitions between sleep states, e.g., REM, S1, S2, S3, and S4, occur based on the monitored physiological parameters, e.g., via the EEG using the circuit 68 discussed above with reference to FIG. 4 (174).

Additionally, while patient 12 is sleeping, IMD 18 monitors physiological parameters of patient 12 (172) to determine whether patient 12 has woken up (176). When IMD 18 determines that patient 12 is awake, IMD 18 identifies the time that patient 12 awoke (178), and determines sleep quality metric values based on the information collected while patient 12 was asleep (180).

For example, one sleep quality metric value IMD 18 may calculate is sleep efficiency, which IMD 18 may calculate as a percentage of time during which patient 12 is attempting to sleep that patient 12 is actually asleep. IMD 18 may determine a first amount of time between the time IMD 18 identified that patient 12 fell asleep and the time IMD 18 identified that patient 12 awoke. IMD 18 may also determine a second amount of time between the time IMD 18 identified that patient 12 began attempting to fall asleep and the time IMD 18 identified that patient 12 awoke. To calculate the sleep efficiency, IMD 18 may divide the first time by the second time.

Another sleep quality metric value that IMD 18 may calculate is sleep latency, which IMD 18 may calculate as the amount of time between the time IMD 18 identified that patient 12 was attempting to fall asleep and the time IMD 18 identified that patient 12 fell asleep. Other sleep quality metrics with values determined by IMD 18 based on the information collected by IMD 18 in the illustrated example include: total time sleeping per day, at night, and during daytime hours; number of apnea and arousal events per occurrence of sleep; and amount of time spent in the various sleep states, e.g., one or both of the S3 and S4 sleep states. IMD 18 may store the determined values as sleep quality metric values 158 within memory 54.

IMD 18 may perform the example method illustrated in FIG. 8 continuously, e.g., may monitor to identify when patient 12 is attempting to sleep and asleep any time of day, each day. In other embodiments, IMD 18 may only perform the method during evening hours and/or once every N days to conserve battery and memory resources. Further, in some embodiments, IMD 18 may only perform the method in response to receiving a command from patient 12 or a clinician via one a programmer 28. For example, patient 12 may direct IMD 18 to collect sleep quality information at times when the patient believes that his or her sleep quality is low or therapy is ineffective.

Figure 9:
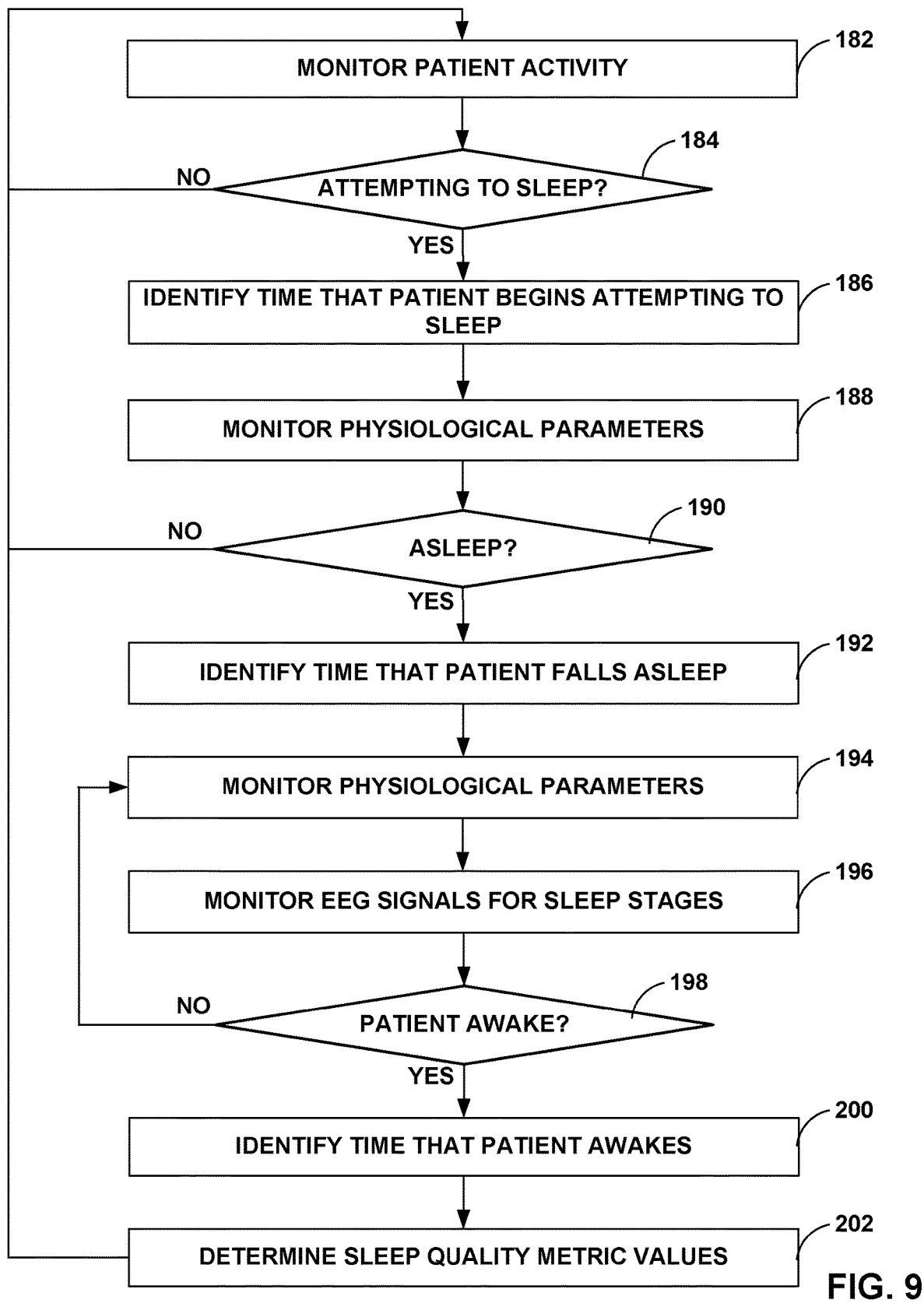
FIG. 9 is a flow diagram illustrating an example method for collecting sleep quality information and sleep type that may be employed by an implantable medical device.

FIG. 9 is a flow diagram illustrating another example method for collecting sleep quality information that may be employed by IMD 18, 32 or 122. IMD 18 will be used as an example, and specifically, IMD 18 uses the EEG signal to determine sleep state. IMD 18 monitors the posture and activity level of patient 12, or monitors for an indication from patient 12, e.g., via programmer 28 (182), and determines whether patient 12 is attempting to fall asleep based on the posture, activity level, melatonin level, and/or a patient indication, as described above (184). If IMD 18 determines that patient 12 is attempting to fall asleep, IMD 18 identifies the time that patient 12 began attempting to fall asleep using any of the techniques described above (186), and monitors one or more of the various physiological parameters of patient 12 discussed above to determine whether patient 12 is asleep (188, 190).

In some embodiments, IMD 18 compares parameter values or parameter variability values to one or more threshold values 156 to determine whether patient 12 is asleep. In other embodiments, IMD 18 applies one or more functions or look-up tables to determine one or more sleep probability metric values based on the physiological parameter values, and compares the sleep probability metric values to one or more threshold values 156 to determine whether patient 12 is asleep.

In some embodiments, IMD 18 analyzes the amplitude and/or frequency of the EEG, alone or in combination with other physiological parameter signals, to determine whether patient is asleep. For example, IMD 18 may analyze one or more of posture, activity, ECG, or other physiological signals discussed above in combination with the EEG, e.g., using sleep probability values for each signal, to determine whether the signals considered in combination indicate that patient 12 is asleep. In some case, circuit 68 may be used to analyze the EEG for this purpose by, for example, indicating that patient 12 is asleep when the patient is within the S1 or S2 sleep states. While monitoring physiological parameters (188) to determine whether patient 12 is asleep (190), IMD 18 may continue to monitor the posture and/or activity level of patient 12 (182) to confirm that patient 12 is still attempting to fall asleep (184).

When IMD 18 determines that patient 12 is asleep, e.g., by analysis of the various parameters contemplated herein, IMD 18 will identify the time that patient 12 fell asleep (192). While patient 12 is sleeping, IMD 18 will continue to monitor physiological parameters of patient 12 (194). As discussed above, IMD 18 may identify the occurrence of arousals and/or apneas based on the monitored physiological parameters (196). Further, IMD 18 may identify the time that patient 12 transitions between sleep states, e.g., REM, S1, S2, S3, and S4, occur based on the monitored physiological parameters, such as by analysis of the EEG signal using circuit 68 discussed above with reference to FIG. 4 (196).

Additionally, while patient 12 is sleeping, IMD 122 monitors physiological parameters of patient 12 (194) to determine whether patient 12 has woken up (198). When IMD 18 determines that patient 12 is awake, IMD 18 identifies the time that patient 12 awoke (200), and determines sleep quality metric values based on the information collected while patient 12 was asleep (202).

For example, one sleep quality metric value IMD 18 may calculate is sleep efficiency, which IMD 18 may calculate as a percentage of time during which patient 12 is attempting to sleep that patient 12 is actually asleep. IMD 18 may determine a first amount of time between the time IMD 18 identified that patient 12 fell asleep and the time IMD 18 identified that patient 12 awoke. IMD 18 may also determine a second amount of time between the time IMD 18 identified that patient 12 began attempting to fall asleep and the time IMD 18 identified that patient 12 awoke. To calculate the sleep efficiency, IMD 18 may divide the first time by the second time.

Another sleep quality metric value that IMD 18 may calculate is sleep latency, which IMD 18 may calculate as the amount of time between the time IMD 18 identified that patient 12 was attempting to fall asleep and the time IMD 18 identified that patient 12 fell asleep. Other sleep quality metrics with values determined by IMD 18 based on the information collected by IMD 18 in the illustrated example include: total time sleeping per day, at night, and during daytime hours; number of apnea and arousal events per occurrence of sleep; and amount of time spent in the various sleep states, e.g., one or both of the S3 and S4 sleep states. IMD 18 may store the determined values as sleep quality metric values 158 within memory 54 or 148.

IMD 18 may perform the example method illustrated in FIG. 9 continuously, e.g., may monitor to identify when patient 12 is attempting to sleep and asleep any time of day, each day. In other embodiments, IMD 18 may only perform the method during evening hours and/or once every N days to conserve battery and memory resources. Further, in some embodiments, IMD 18 may only perform the method in response to receiving a command from patient 12 or a clinician via programmer 28 or one of programmers 128, 134. For example, patient 12 may direct IMD 18 to collect sleep quality information at times when the patient believes that his or her sleep quality is low or therapy is ineffective.

Figure 10:
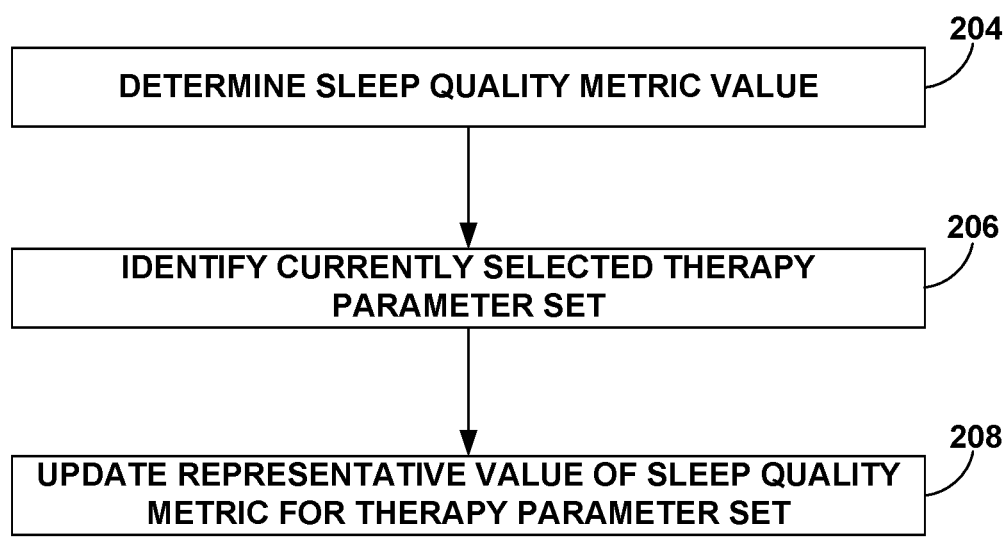
FIG. 10 is a flow diagram illustrating an example method for associating sleep quality information with therapy parameter sets that may be employed by an implantable medical device.

FIG. 10 is a flow diagram illustrating an example method for associating sleep quality information with therapy parameter sets 152 that may be employed by and IMDs 18, 32 or 122. IMD 18 will be used herein as an example. IMD 18 determines a value of a sleep quality metric according to any of the techniques described above (204). IMD 18 also identifies the current therapy parameter set, e.g., the therapy parameter set 152 used by IMD 18 to control delivery of therapy when patient 12 was asleep (206), and associates the newly determined value with the current therapy parameter set 152.

Among sleep quality metric values 158 within memory 54, IMD 18 stores a representative value of the sleep quality metric, e.g., a mean or median value, for each of the plurality of therapy parameter sets 152. IMD 18 updates the representative values for the current therapy parameter set based on the newly determined value of the sleep quality metric. For example, a newly determined sleep efficiency value may be used to determine a new average sleep efficiency value for the current therapy parameter set 152.

Figure 11:
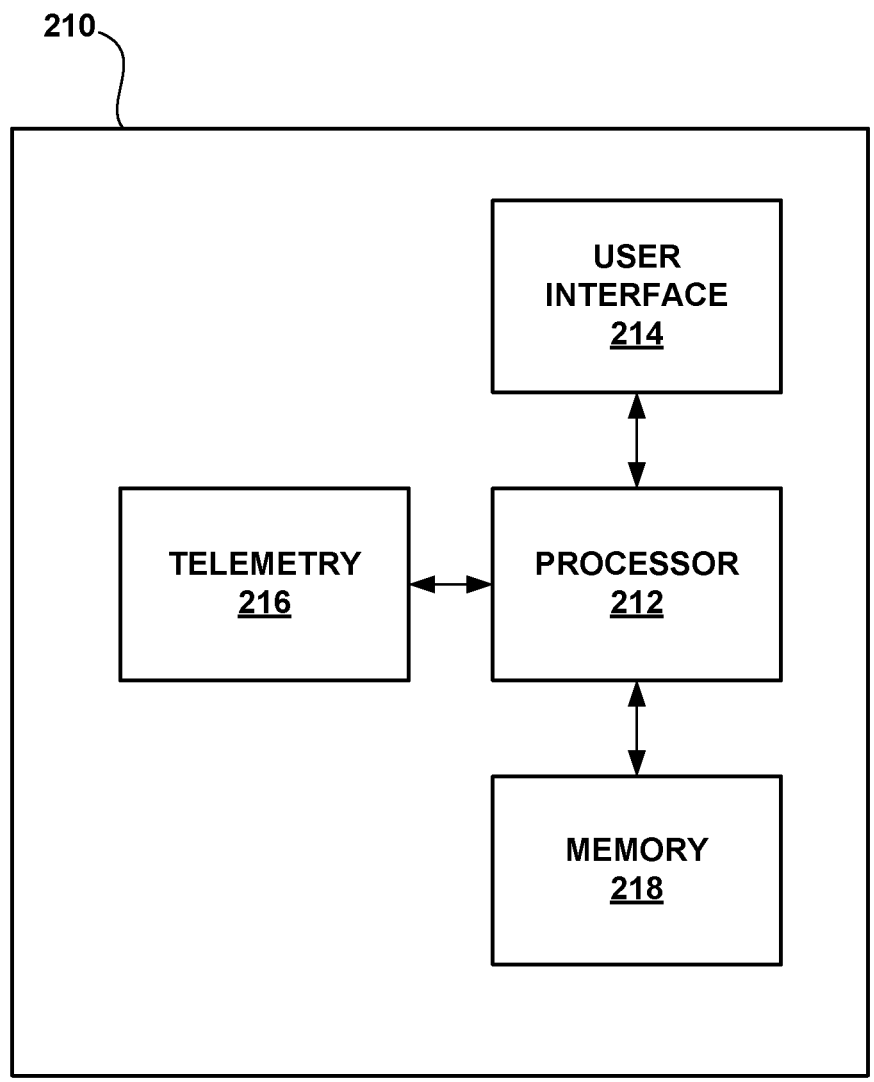
FIG. 11 is a block diagram illustrating an example clinician programmer.

FIG. 11 is a block diagram further illustrating clinician programmer 210. Clinician programmer 210 may be an embodiment of any programmers 28 or 128. A clinician may interact with a processor 212 via a user interface 214 in order to program therapy for patient 12. Further, processor 212 may receive sleep quality metric values 158 from IMD 122 via a telemetry circuit 216, and may generate sleep quality information for presentation to the clinician via user interface 214. User interface 214 may include a display and keypad, such as display 130 and keypad 132 of programmer 128, and may also include a touch screen or peripheral pointing devices as described above. Processor 212 may include a microprocessor, a controller, a DSP, an ASIC, an FPGA, discrete logic circuitry, or the like.

Clinician programmer 210 also includes a memory 218. Memory 218 may include program instructions that, when executed by processor 212, cause clinician programmer 210 to perform the functions ascribed to clinician programmers 28 or 128 herein. Memory 218 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 12:
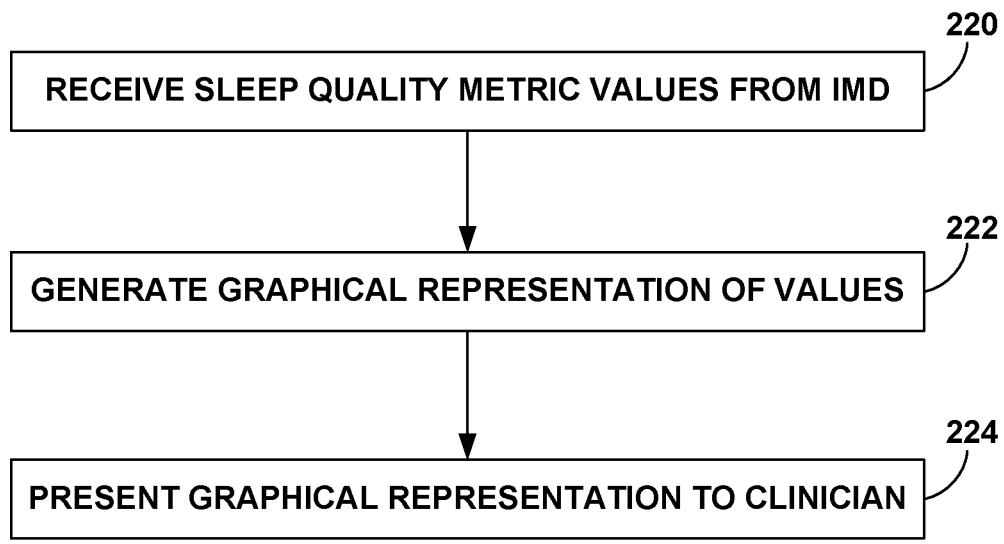
FIG. 12 is a flow diagram illustrating an example method for presenting sleep quality information to a clinician that may be employed by a clinician programmer.

FIG. 12 is a flow diagram illustrating an example method for presenting sleep quality information to a clinician that may be employed by clinician programmer 210, e.g., programmers 28 or 128. Clinician programmer 210 receives sleep quality metric values 158 from IMD 122, e.g., via telemetry circuit 216 (220). The sleep quality metric values 158 may be daily values, or mean or median values determined over greater periods of time, e.g., weeks or months.

Clinician programmer 210 may simply present the values to the clinician via a display, in any form, such as a table of average values, or clinician programmer 210 may generate a graphical representation of the sleep quality metric values (222). For example, clinician programmer 210 may generate a trend diagram illustrating sleep quality metric values 158 over time, or a histogram, pie chart, or other graphic illustration of percentages of sleep quality metric values 158 collected by IMD 122 that were within ranges. Where clinician programmer 210 generates a graphical representation of the sleep quality metric values 158, clinician programmer 210 presents the graphical representation to the clinician via the display (224).

FIG. 13 illustrates an example list 226 of therapy parameter sets and associated sleep quality metric values that may be presented to a clinician by clinician programmer 210. Each row of example list 226 includes an identification of one of therapy parameter sets 152, the parameters of the set, and a representative value for one or more sleep quality metrics associated with the identified therapy parameter set, such as sleep efficiency, sleep latency, or both. The example list 226 includes representative values for sleep efficiency, sleep latency, and "deep sleep," e.g., the average amount of time per night spent in either of the S3 and S4 sleep states.

Figure 14:
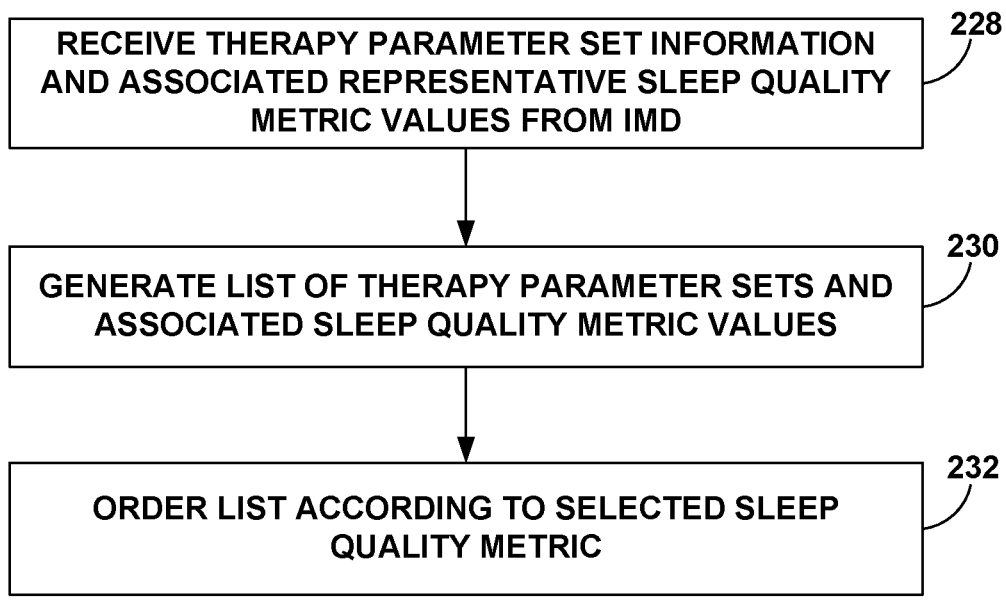
FIG. 14 is a flow diagram illustrating an example method for displaying a list of therapy parameter sets and associated sleep quality information that may be employed by a clinician programmer.

FIG. 14 is a flow diagram illustrating an example method for displaying a list 226 of therapy parameter sets and associated sleep quality information that may be employed by clinician programmer 210. According to the example method, clinician programmer 210 receives information identifying the plurality of therapy parameter sets 152 stored in memory 148 of IMD 122 (or memory 54 of IMD 18, 32), and one or more representative sleep quality metric values associated with each of the therapy parameter sets (228). Clinician programmer 210 generates a list 226 of the therapy parameter sets 152 and any associated representative sleep quality metric values (230), and orders the list according to a selected sleep quality metric (232). For example, in the example list 226 illustrated in FIG. 13, the clinician may select whether list 226 should be ordered according to sleep efficiency or sleep latency via user interface 214 of clinician programmer 210.

Figure 15:
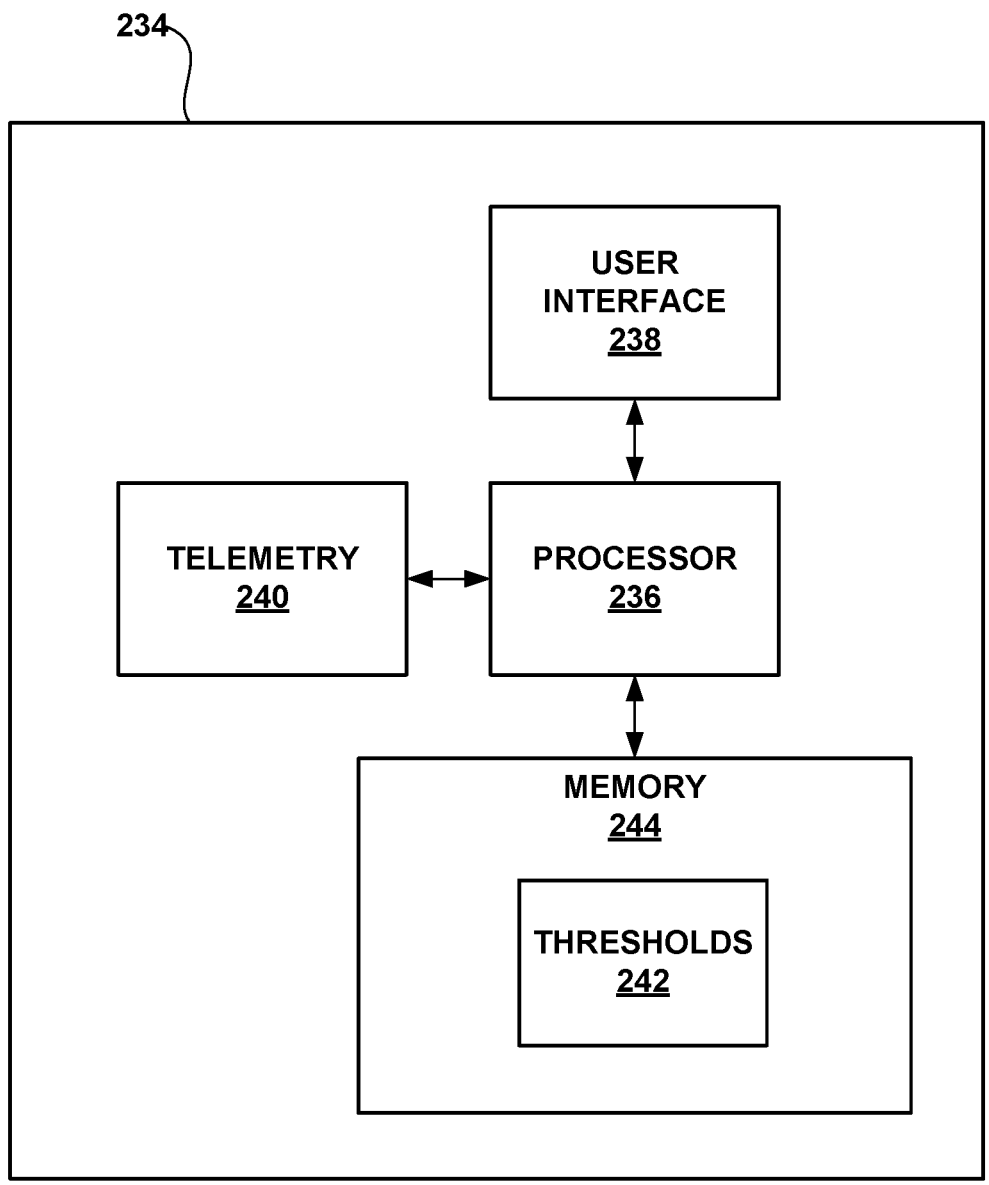
FIG. 15 is a block diagram illustrating an example patient programmer.

FIG. 15 is a block diagram further illustrating patient programmer 234. Patient programmer 234 may be an embodiment of programmers 28 or 134. Patient 12 may interact with a processor 236 via a user interface 238 in order to control delivery of therapy, i.e., select or adjust one or more of therapy parameter sets 152 stored by IMD 122 (or IMDs 18 and 32). Processor 236 may also receive sleep quality metric values 158 from IMD 122 via a telemetry circuit 240, and may provide messages related to sleep quality to patient 12 via user interface 238 based on the received values. User interface 238 may include a display and keypad, such as display 28 and keypad 30 of patient programmer 134, and may also include a touch screen or peripheral pointing devices as described above.

In some embodiments, processor 236 may determine whether to provide a message related to sleep quality to patient 12 based on the received sleep quality metric values. For example, processor 236 may periodically receive sleep quality metric values 158 from IMD 122 when placed in telecommunicative communication with IMD 122 by patient 12, e.g., for therapy selection or adjustment. Processor 236 may compare these values to one or more thresholds 242 stored in a memory 244 to determine whether the quality of the patient's sleep is poor enough to warrant a message.

Processor 236 may present messages to patient 12 as text via display, and/or as audio via speakers included as part of user interface 238. The message may, for example, direct patient 12 to see a physician, increase therapy intensity before sleeping, or select a different therapy parameter set before sleeping than the patient had typically selected previously. In some embodiments, the message may indicate the quality of sleep to patient 12 to, for example, provide patient 12 with an objective indication of whether his or her sleep quality is good, adequate, or poor. Further, in some embodiments, processor 236 may, like clinician programmer 210, receive representative sleep quality metric values. In such embodiments, processor 236 may identify a particular one or more of therapy parameter sets 152 to recommend to patient 12 based on representative sleep quality metric values associated with those programs.

Processor 236 may include a microprocessor, a controller, a DSP, an ASIC, an FPGA, discrete logic circuitry, or the like. Memory 244 may also include program instructions that, when executed by processor 236, cause patient programmer 234 to perform the functions ascribed to patient programmer 234 herein. Memory 244 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 16:
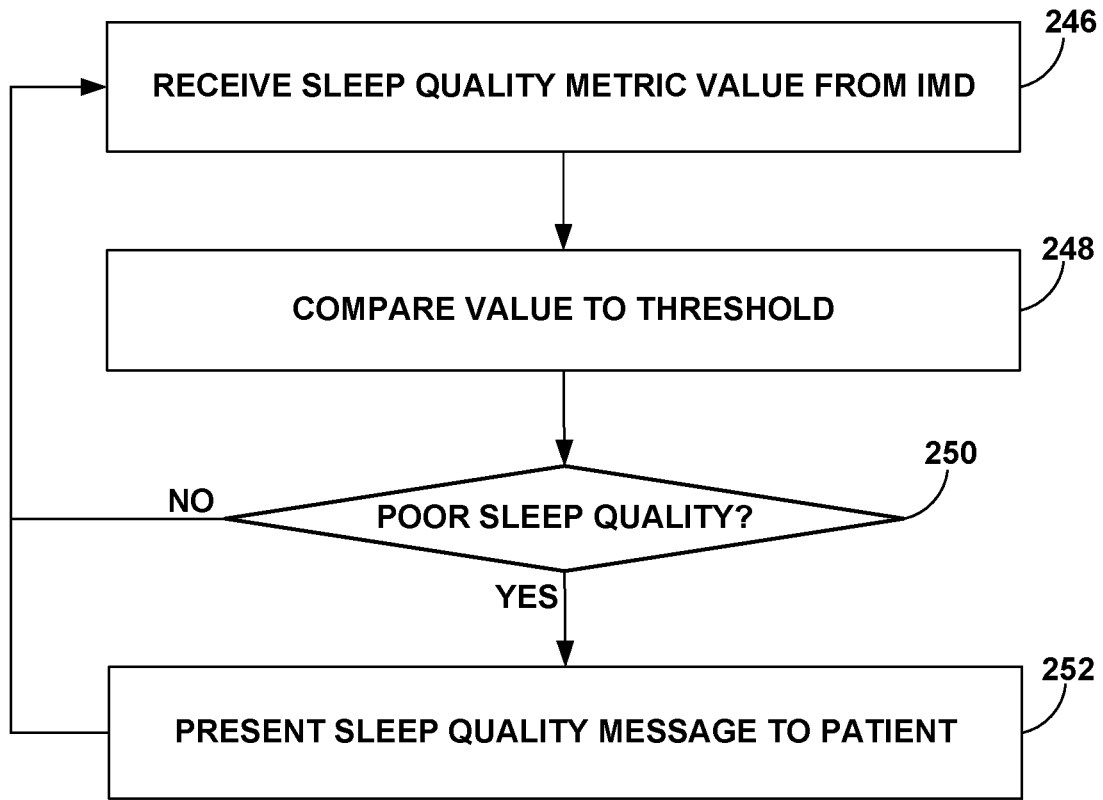
FIG. 16 is a flow diagram illustrating an example method for presenting a sleep quality message to a patient that may be employed by a patient programmer.

FIG. 16 is a flow diagram illustrating an example method for presenting a sleep quality message to patient 12 that may be employed by patient programmer 234, e.g., programmers 28 or 134. According to the illustrated example method, patient programmer 234 receives a sleep quality metric value from IMD 122 (or IMDs 18 or 32) (246), and compares the value to a threshold value 242 (248). Patient programmer 234 determines whether the comparison indicates poor sleep quality (250). If the comparison indicates that the quality of sleep experienced by patient 12 is poor, patient programmer 234 presents a message related to sleep quality to patient 12 (252).

Various embodiments of the invention have been described. However, one skilled in the art will recognize that various modifications may be made to the described embodiments without departing from the scope of the invention. For example, although described herein primarily in the context of treatment of pain with an implantable neurostimulator, the invention is not so limited. The invention may be embodied in any implantable medical device, such as a cardiac pacemaker, an implantable pump, or an implantable monitor that does not itself deliver a therapy to the patient. Further, the invention may be implemented via an external, e.g., non-implantable, medical device.

As discussed above, the ability of a patient to experience quality sleep, e.g., the extent to which the patient able to achieve adequate periods of undisturbed sleep in deeper, more restful sleep states, may be negatively impacted by any of a variety of ailments or symptoms. Accordingly, the sleep quality of a patient may reflect the progression, status, or severity of the ailment or symptom. Further, the sleep quality of the patient may reflect the efficacy of a particular therapy or therapy parameter set in treating the ailment or symptom. In other words, it may generally be the case that the more efficacious a therapy or therapy parameter set is, the higher quality of sleep the patient will experience.

As discussed above, in accordance with the invention, sleep quality metrics may be monitored, and used to evaluate the status, progression or severity of an ailment or symptom, or the efficacy of therapies or therapy parameter sets used to treat the ailment or symptom. As an example, epileptic seizures may disturb a patient's sleep, and poor sleep may lead to more frequent or severe seizures.

In some embodiments, systems according to the invention may include any of a variety of medical devices that deliver any of a variety of therapies to treat epilepsy, such as DBS, or one or more drugs, or cooling therapy. Systems may use the techniques of the invention described above to determine sleep quality metrics for the patient and evaluate such therapies, e.g., by associating sleep quality metrics with therapy parameter sets for delivery of such therapies. Systems according to the invention may thereby evaluate the extent to which a therapy or therapy parameter set is alleviating epilepsy by evaluating the extent to which the therapy or therapy parameter set improves sleep quality for the patient.

As another example, chronic pain may cause a patient to have difficulty falling asleep, experience arousals during sleep, or have difficulty experiencing deeper sleep states. Systems according to the invention may monitor sleep quality metrics to evaluate the extent to which the patient is experiencing pain.

In some embodiments, systems according to the invention may include any of a variety of medical devices that deliver any of a variety of therapies to treat chronic pain, such as SCS, DBS, cranial nerve stimulation, peripheral nerve stimulation, or one or more drugs. Systems may use the techniques of the invention described above to determine sleep quality metrics for the patient and evaluate such therapies, e.g., by associating sleep quality metrics with therapy parameter sets for delivery of such therapies. Systems according to the invention may thereby evaluate the extent to which a therapy or therapy parameter set is alleviating chronic pain by evaluating the extent to which the therapy or therapy parameter set improves sleep quality for the patient.

As another example, psychological disorders may cause a patient to experience low sleep quality. Accordingly, embodiments of the invention may determine sleep quality metrics to track the status or progression of a psychological disorder, such as depression, mania, bipolar disorder, or obsessive-compulsive disorder. Further, systems according to the invention may include any of a variety of medical devices that deliver any of a variety of therapies to treat a psychological disorder, such as DBS, cranial nerve stimulation, peripheral nerve stimulation, vagal nerve stimulation, or one or more drugs. Systems may use the techniques of the invention described above to associate sleep quality metrics with the therapies or therapy parameter sets for delivery of such therapies, and thereby evaluate the extent to which a therapy or therapy parameter set is alleviating the psychological disorder by evaluating the extent to which the therapy parameter set improves the sleep quality of the patient.

Movement disorders, such as tremor, Parkinson's disease, multiple sclerosis, and spasticity may also affect the sleep quality experienced by a patient. The uncontrolled movements, e.g., tremor or shaking, associated such disorders, particularly in the limbs, may cause a patient to experience disturbed sleep. Accordingly, systems according to the invention may monitor sleep quality metrics to determine the state or progression of a movement disorder.

Further, systems according to the invention may include any of a variety of medical devices that deliver any of a variety of therapies to treat movement disorders, such as DBS, cortical stimulation, or one or more drugs. Baclofen, which may or may not be intrathecally delivered, is an example of a drug that may be delivered to treat movement disorders. Systems may use the techniques of the invention described above to associate sleep quality metrics with therapies or therapy parameter sets for delivery of such therapies. In this manner, such systems may allow a user to evaluate the extent to which a therapy or therapy parameter set is alleviating the movement disorder by evaluating the extent to which the therapy parameter set improves the sleep quality experienced by the patient.

Additionally, the invention is not limited to embodiments in which a programming device receives information from the medical device, or presents information to a user. Other computing devices, such as handheld computers, desktop computers, workstations, or servers may receive information from the medical device and present information to a user as described herein with reference to programmers 28, 128 or 134. A computing device, such as a server, may receive information from the medical device and present information to a user via a network, such as a local area network (LAN), wide area network (WAN), or the Internet. In some embodiments, the medical device is an external medical device, and may itself include a display to present information to a user.

As another example, the invention may be embodied in a trial neurostimulator, which is coupled to percutaneous leads implanted within the patient to determine whether the patient is a candidate for neurostimulation, and to evaluate prospective neurostimulation therapy parameter sets. Similarly, the invention may be embodied in a trial drug pump, which is coupled to a percutaneous catheter implanted within the patient to determine whether the patient is a candidate for an implantable pump, and to evaluate prospective therapeutic agent delivery parameter sets. Sleep quality metric values collected by the trial neurostimulator or pump may be used by a clinician to evaluate the prospective therapy parameter sets, and select parameter sets for use by the later implanted non-trial neurostimulator or pump. In particular, a trial neurostimulator or pump may determine representative values of one or more sleep quality metrics for each of a plurality of prospective therapy parameter sets, and a computing device, such as a clinician programmer, may present a list of prospective parameter sets and associated representative values to a clinician. The clinician may use the list to identify potentially efficacious parameter sets, and may program a permanent implantable neurostimulator or pump for the patient with the identified parameter sets.

Further, the invention is not limited to embodiments in which an implantable or external medical device that delivers therapy to a patient determines sleep quality metric values. Instead a medical device according to the invention may record values for one or more physiological parameters, and provide the physiological parameter values to a computing device, such as one or both of programmers 28, 128 or 134. In such embodiments, the computing device, and more particularly a processor of the computing device, e.g., processors 212, 236, employs any of the techniques described herein with reference to IMDs 18, 32, and 122 in order to determine sleep quality metric values based on the physiological parameter values received from the medical device. The computing device may receive physiological parameter values from the medical device in real time, or may monitor physiological parameters of the patient by receiving and analyzing physiological parameter values recorded by the medical device over a period of time. In some embodiments, in addition to physiological parameter values, the medical device provides the computing device information identifying times at which the patient indicated that he or she was attempting to fall asleep, which the computing device may use to determine one or more sleep quality metric values as described herein.

In some embodiments, the medical device may associate recorded physiological parameter values with current therapy parameter sets. The medical device may provide information indicating the associations of recorded physiological parameter values and therapy parameter sets to the computing device, e.g., programmer 28, 128 or 134. The computing device may determine sleep quality metric values and representative sleep quality metric values for each of the plurality of therapy parameter sets based on the physiological parameter values associated with the therapy parameter sets, as described herein with reference to IMDs 18, 32, and 122.

Additionally, the invention is not limited to embodiments in which the therapy delivering medical device monitors the physiological parameters of the patient described herein. In some embodiments, a separate monitoring device monitors values of one or more physiological parameters of the patient instead of, or in addition to, a therapy delivering medical device. The monitor may include a processor 146 and memory 148, and may be coupled to sensors 142, as illustrated above with reference to IMD 122 and FIGS. 6 and 7. The monitor may identify sleep quality metric values based on the values of the monitored physiological parameter values, or may transmit the physiological parameter values to a computing device for determination of the sleep quality metric values. In some embodiments, an external computing device, such as a programming device, may incorporate the monitor.

Figure 17:
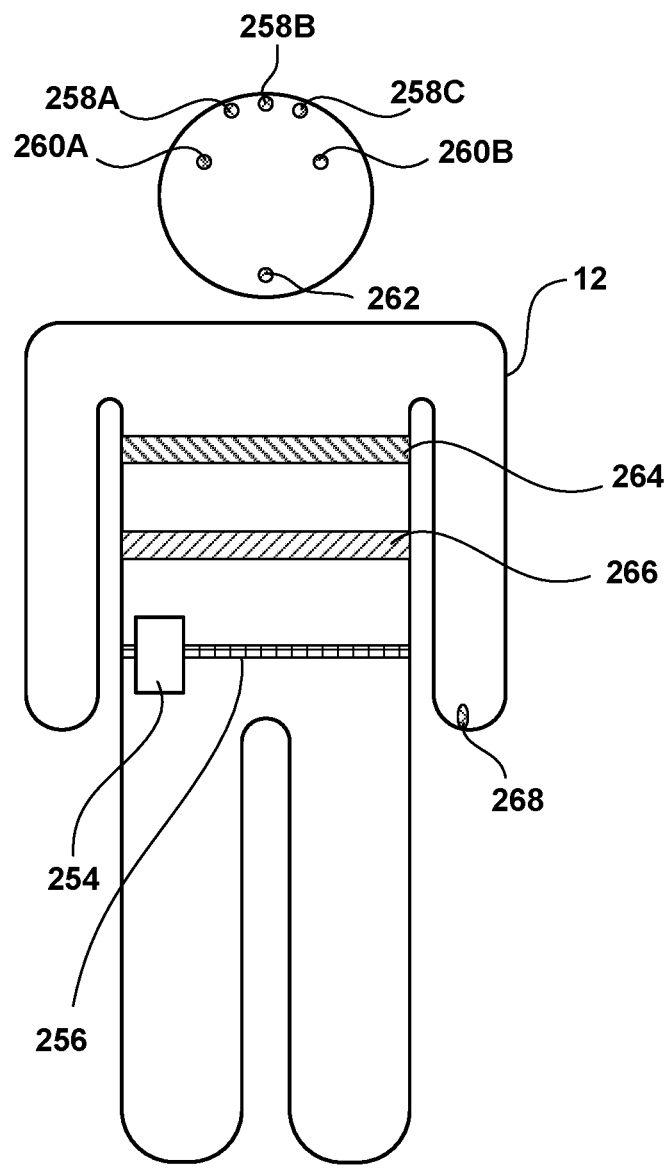
FIG. 17 is a conceptual diagram illustrating a monitor that monitors values of one or more physiological parameters of the patient instead of, or in addition to, a therapy delivering medical device.

FIG. 17 is a conceptual diagram illustrating a monitor 254 that monitors values of one or more physiological parameters of the patient instead of, or in addition to, a therapy delivering medical device such as any of IMDs 18, 32 or 122. In the illustrated example, monitor 254 is configured to be attached to or otherwise carried by a belt 256, and may thereby be worn by patient 12. FIG. 6 also illustrates various sensors 142 that may be coupled to monitor 254 by leads, wires, cables, or wireless connections, such as EEG electrodes 258A-C placed on the scalp of patient 12, a plurality of EOG electrodes 260A and 260B placed proximate to the eyes of patient 12, and one or more EMG electrodes 262 placed on the chin or jaw the patient. The number and positions of electrodes 258, 260 and 262 illustrated in FIG. 17 are merely exemplary. For example, although only three EEG electrodes 258 are illustrated in FIG. 17, an array of between 16 and 25 EEG electrodes 258 may be placed on the scalp of patient 12, as is known in the art. EEG electrodes 258 may be individually placed on patient 12, or integrated within a cap or hair net worn by the patient.

In the illustrated example, patient 12 wears an ECG belt 264. ECG belt 264 incorporates a plurality of electrodes for sensing the electrical activity of the heart of patient 12. The heart rate and, in some embodiments, ECG morphology of patient 12 may monitored by monitor 254 based on the signal provided by ECG belt 264. Examples of suitable belts 264 for sensing the heart rate of patient 12 are the "M" and "F" heart rate monitor models commercially available from Polar Electro. In some embodiments, instead of belt 264, patient 12 may wear a plurality of ECG electrodes attached, e.g., via adhesive patches, at various locations on the chest of the patient, as is known in the art. An ECG signal derived from the signals sensed by such an array of electrodes may enable both heart rate and ECG morphology monitoring, as is known in the art.

As shown in FIG. 17, patient 12 may also wear a respiration belt 266 that outputs a signal that varies as a function of respiration of the patient. Respiration belt 266 may be a plethysmograpy belt, and the signal output by respiration belt 266 may vary as a function of the changes is the thoracic or abdominal circumference of patient 12 that accompany breathing by the patient. An example of a suitable belt 266 is the TSD201 Respiratory Effort Transducer commercially available from Biopac Systems, Inc. Alternatively, respiration belt 266 may incorporate or be replaced by a plurality of electrodes that direct an electrical signal through the thorax of the patient, and circuitry to sense the impedance of the thorax, which varies as a function of respiration of the patient, based on the signal. In some embodiments, ECG and respiration belts 264 and 266 may be a common belt worn by patient 12, and the relative locations of belts 264 and 266 depicted in FIG. 17 are merely exemplary.

In the example illustrated by FIG. 17, patient 12 also wears a transducer 268 that outputs a signal as a function of the oxygen saturation of the blood of patient 12. Transducer 268 may be an infrared transducer. Transducer 268 may be located on one of the fingers or earlobes of patient 12. Sensors 142 coupled to monitor 254 may additionally or alternatively include any of the variety of sensors described above that monitor any one or more of activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response.

The invention may also be embodied as a computer-readable medium that includes instructions to cause a processor to perform any of the methods described herein. These and other embodiments are within the scope of the following claims.

What is claimed is:

1. A method comprising:
   delivering a therapy from a medical device according to a first set of therapy parameters within a cranium of a patient to treat a neurological disorder of the patient;
   sensing, via at least one electrode of a lead positioned within the cranium of the patient, electrical activity of the brain of the patient during the delivery of the therapy to the patient according to the first set of therapy parameters, the at least one electrode being in communication with the medical device;
   associating each of a plurality of different frequency bands of the sensed electrical activity of the brain of the patient with a respective one or more sleep states of a plurality of sleep states of the patient, wherein the plurality of sleep states comprise at least two of a rapid eye movement (REM) state, a non-rapid eye movement (NREM) S1 state, an NREM S2 state, an NREM S3 state, or an NREM S4 state;
   comparing the relative power levels of the plurality of different frequency bands of the sensed electrical activity of the brain of the patient to one another;
   determining that a first relative power of a first frequency band of the plurality of different frequency bands is greater than a relative power of each of the other frequency bands of the plurality of different frequency bands;
   determining, based upon the determination that the first relative power of the first frequency band is greater than the relative power of each of the other frequency bands, that the patient is within a first sleep state of the plurality of sleep states associated with the first frequency band;
   selecting a second set of therapy parameters for the delivery of the therapy based on the determination that the patient is within the first sleep state; and
   after delivering the therapy according to the first set of therapy parameters, delivering the therapy according to the second set of therapy parameters.

2. The method of claim 1, further comprising presenting a message related to sleep quality of the patient via a patient programmer based on the determination that the patient is within the first sleep state of the plurality of sleep states.

3. The method of claim 1, wherein delivering therapy comprises delivering the therapy according to a plurality of therapy parameter sets, the plurality of therapy parameter sets comprising the first set of therapy parameters and the second set of therapy parameters, the method further comprising associating, for each of the plurality of therapy parameter sets, a particular therapy parameter set of the plurality of therapy parameter sets with each sleep state of the plurality of states based on electrical activity of the brain during the delivery of the therapy according to the particular therapy parameter set.

4. The method of claim 1, wherein delivering the therapy comprises delivering at least one of an epilepsy therapy, a movement disorder therapy, or a psychological disorder therapy.

5. The method of claim 1, wherein delivering the therapy comprises delivering deep brain stimulation (DBS).

6. The method of claim 1, wherein delivering the therapy comprises delivering a therapy according to a plurality of therapy parameter sets, the plurality of therapy parameter sets comprising the first set of therapy parameters and the second set of therapy parameters, the method further comprising selecting different therapy parameter sets for the therapy from the medical device based on the determination that the patient is within the first sleep state.

7. The method of claim 1, wherein one of the frequency bands of the plurality of different frequency bands includes frequencies between 30 Hz and approximately 50 Hz.

* * * * *